(12) United States Patent
Mirza et al.

(10) Patent No.: US 10,265,093 B2
(45) Date of Patent: *Apr. 23, 2019

(54) COMPACT ENDOSCOPIC SURGICAL BLADE ASSEMBLY AND METHOD OF USE THEREOF

(71) Applicant: A.M. SURGICAL, INC., Smithtown, NY (US)

(72) Inventors: Romi Mirza, Smithtown, NY (US); Ather Mirza, Smithtown, NY (US)

(73) Assignee: A.M. SURGICAL, INC., Smithtown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/433,702

(22) Filed: Feb. 15, 2017

(65) Prior Publication Data
US 2017/0172598 A1    Jun. 22, 2017

Related U.S. Application Data

(63) Continuation of application No. 15/206,238, filed on Jul. 9, 2016, now Pat. No. 9,610,089, which is a
(Continued)

(51) Int. Cl.
*A61B 17/32* (2006.01)
*A61B 90/00* (2016.01)
(Continued)

(52) U.S. Cl.
CPC ........ *A61B 17/32002* (2013.01); *A61B 1/317* (2013.01); *A61B 17/320016* (2013.01);
(Continued)

(58) Field of Classification Search
CPC ...... A61B 17/320016; A61B 17/32002; A61B 17/320036; A61B 2017/320008; A61B 2017/320028
(Continued)

(56) References Cited

U.S. PATENT DOCUMENTS 5,447,513 A    9/1995  Davison et al.
5,569,283 A   10/1996  Green et al.
(Continued)

OTHER PUBLICATIONS

International Search Report and Written Opinion issued in International Patent Application No. PCT/US2013/029831 dated Jun. 26, 2013.
(Continued)

*Primary Examiner* — David C Eastwood
*Assistant Examiner* — Erich Herbermann
(74) *Attorney, Agent, or Firm* — Ping Wang; Morris, Manning & Martin, LLP

(57) ABSTRACT

An endoscopic surgical device comprising a slotted clear cannula, a blade and a housing, wherein the cannula is attached to the housing, and wherein the blade is enclosed in the housing and is slidable into the cannula is disclosed. The blade is enclosed within the housing and cannula, and has a horizontally-oriented pushing component and a vertically-oriented cutting component that protrudes through the slot of the cannula. A method for a performing an operative procedure on a target tissue in a subject using the endoscopic surgical device is also described.

15 Claims, 26 Drawing Sheets

Related U.S. Application Data continuation of application No. 14/936,064, filed on Nov. 9, 2015, now Pat. No. 9,408,623, which is a continuation of application No. 14/820,263, filed on Aug. 6, 2015, now Pat. No. 9,211,136, which is a continuation of application No. 14/640,930, filed on Mar. 6, 2015, now Pat. No. 9,179,930, which is a continuation of application No. 14/304,621, filed on Jun. 13, 2014, now Pat. No. 8,979,880, which is a continuation of application No. 13/790,016, filed on Mar. 8, 2013, now Pat. No. 8,911,470, which is a continuation-in-part of application No. 13/602,968, filed on Sep. 4, 2012.

(51) Int. Cl.
*A61B 1/317* (2006.01)
*A61B 17/00* (2006.01)
*A61B 17/3211* (2006.01)

(52) U.S. Cl.
CPC ...... *A61B 17/320036* (2013.01); *A61B 90/02* (2016.02); *A61B 2017/00389* (2013.01); *A61B 2017/00393* (2013.01); *A61B 2017/00424* (2013.01); *A61B 2017/00907* (2013.01); *A61B 2017/320008* (2013.01); *A61B 2017/320028* (2013.01); *A61B 2017/320044* (2013.01); *A61B 2017/32113* (2013.01); *A61B 2090/035* (2016.02)

(58) Field of Classification Search
USPC .............. 606/170–172, 1, 79–85, 167, 185; 600/564, 106, 104, 570; 7/158; 81/439, 81/440; 30/162, 163, 152
See application file for complete search history.

(56) References Cited

U.S. PATENT DOCUMENTS

| | | | |
|---|---|---|---|
| 5,595,410 | A | 1/1997 | Wilson et al. |
| 5,755,713 | A * | 5/1998 | Bilof ................ A61B 17/00234 600/104 |
| 6,138,537 | A * | 10/2000 | Cole ........................ B25F 1/04 81/437 |
| 2004/0098005 | A1 | 5/2004 | Mirza et al. |
| 2006/0053986 | A1 * | 3/2006 | Ward ..................... B25G 1/085 81/490 |
| 2007/0288043 | A1 | 12/2007 | Rehnke |
| 2008/0045989 | A1 | 2/2008 | Welborn |
| 2008/0065124 | A1 | 3/2008 | Olson |
| 2009/0043270 | A1 | 2/2009 | Noyce |
| 2010/0069936 | A1 | 3/2010 | Palmer et al. |
| 2010/0228085 | A1 | 9/2010 | Mirza et al. |
| 2011/0046652 | A1 * | 2/2011 | Rehnke .................. A61B 1/313 606/170 |
| 2011/0046710 | A1 | 2/2011 | Mangiardi et al. |
| 2011/0120779 | A1 | 5/2011 | Siepi |
| 2011/0130779 | A1 * | 6/2011 | Mirza .................... A61B 1/018 606/170 |

OTHER PUBLICATIONS

File history of U.S. Appl. No. 13/602,968, filed Sep. 4, 2012.
File history of U.S. Appl. No. 13/790,016, filed Mar. 8, 2013.
File history of U.S. Appl. No. 14/304,621, filed Jun. 13, 2014.
File history of U.S. Appl. No. 14/640,930, filed Mar. 6, 2015.
File history of U.S. Appl. No. 14/820,263, filed Aug. 6, 2015.
File history of U.S. Appl. No. 14/936,064, filed Nov. 9, 2015.
File history of U.S. Appl. No. 15/206,238, filed Jul. 9, 2016.

* cited by examiner

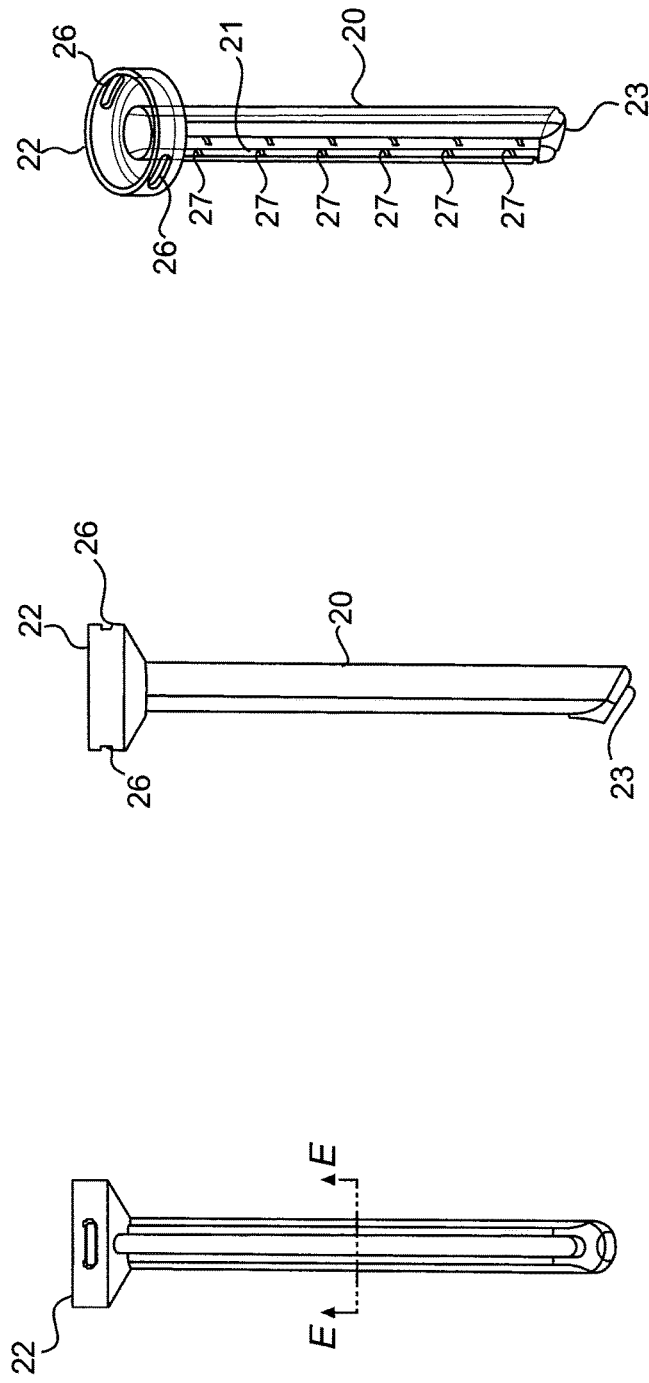

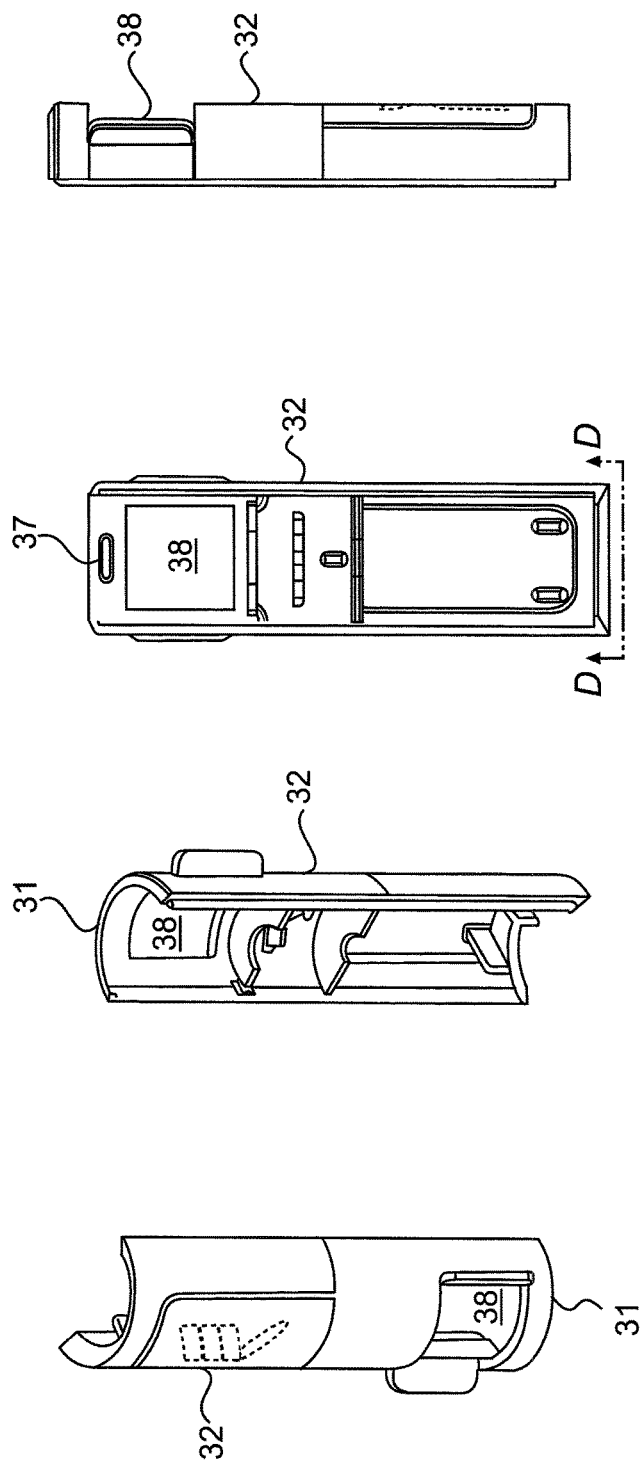

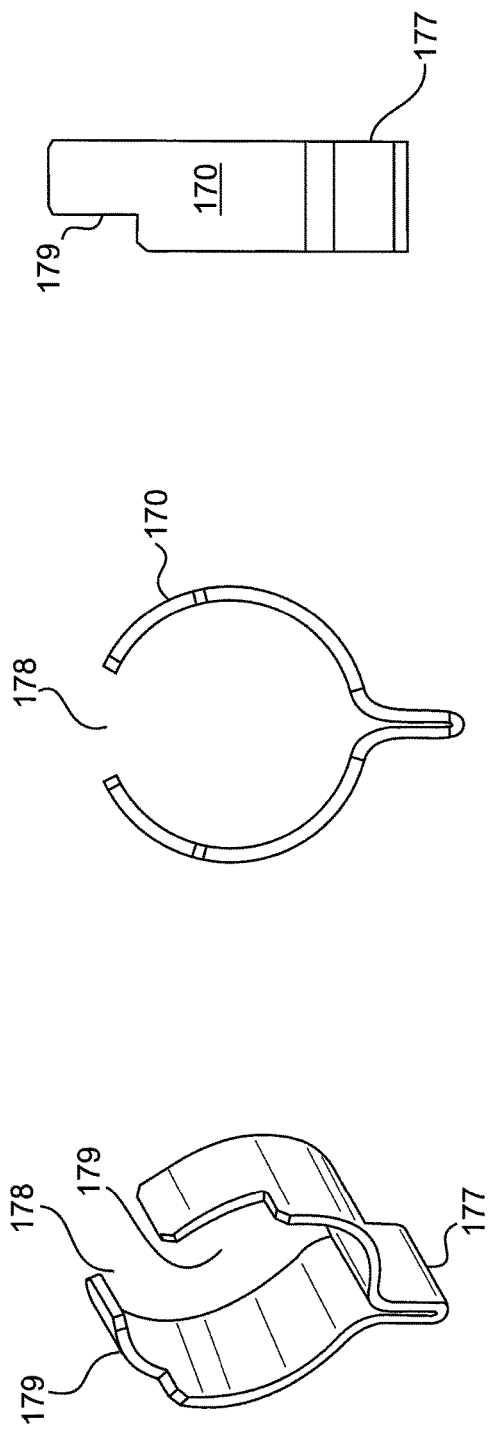

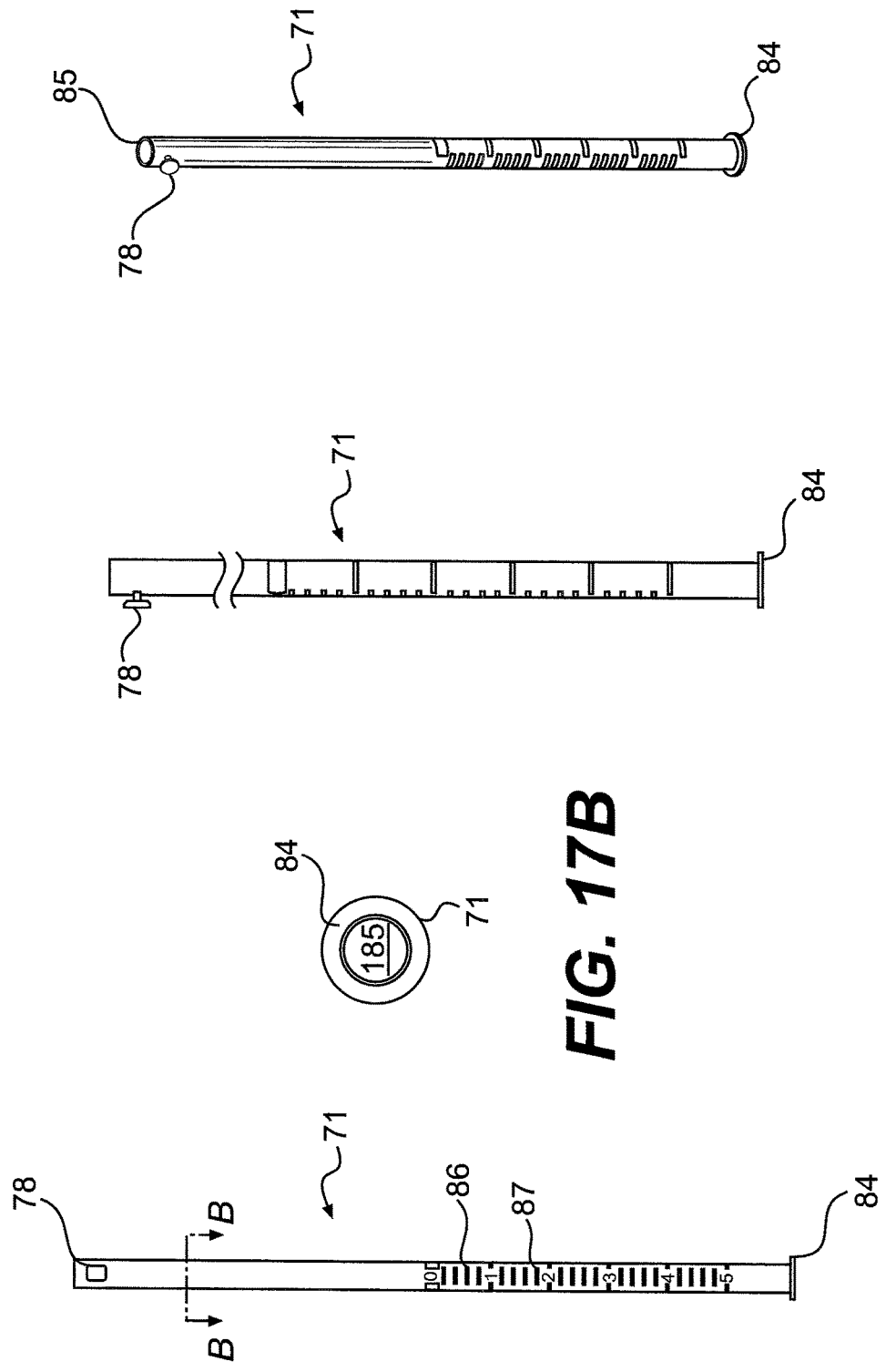

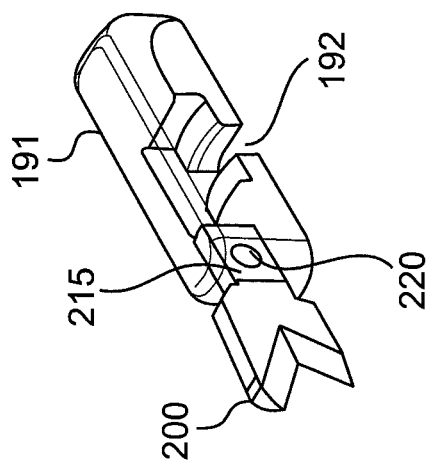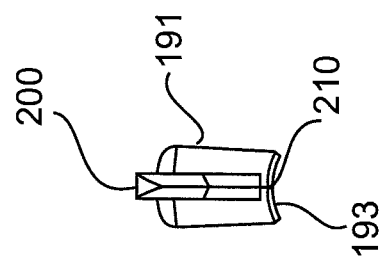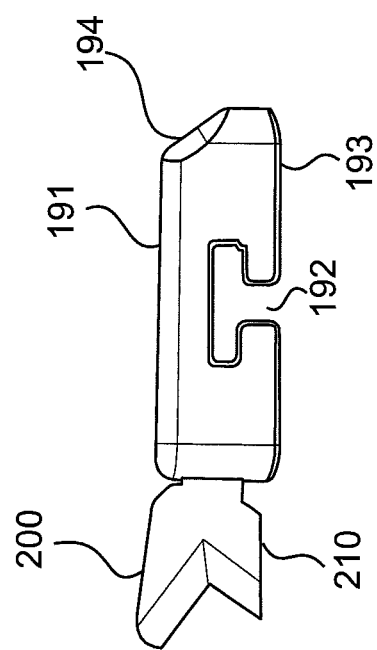

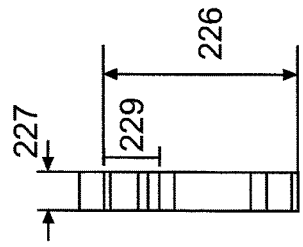
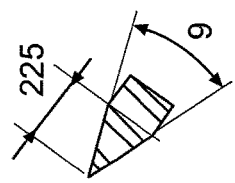
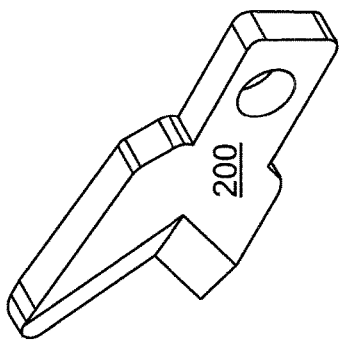
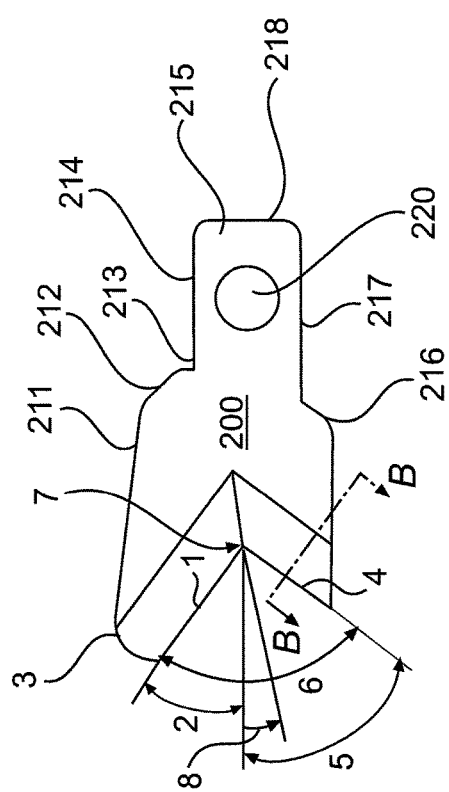
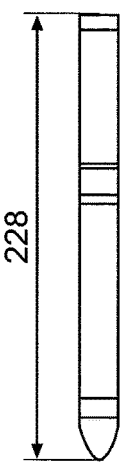
FIG. 19C
FIG. 19B
FIG. 19E
FIG. 19A
FIG. 19D

COMPACT ENDOSCOPIC SURGICAL BLADE ASSEMBLY AND METHOD OF USE THEREOF

This application is a continuation application of U.S. patent application Ser. No. 15/206,238, filed on Jul. 9, 2016, which is a continuation application of U.S. patent application Ser. No. 14/936,064, filed on Nov. 9, 2015, now U.S. Pat. No. 9,408,623, which is a continuation application of U.S. patent application Ser. No. 14/820,263, filed on Aug. 6, 2015, now U.S. Pat. No. 9,211,136, which is a continuation application of U.S. patent application Ser. No. 14/640,930, filed on Mar. 6, 2015, now U.S. Pat. No. 9,179,930, is a continuation application of U.S. patent application Ser. No. 14/304,621, filed on Jun. 13, 2014, now U.S. Pat. No. 8,979,880, which is a continuation application of U.S. patent application Ser. No. 13/790,016, filed on Mar. 8, 2013, now U.S. Pat. No. 8,911,470, which is a continuation-in-part application of U.S. patent application Ser. No. 13/602,968, filed on Sep. 4, 2012. The entirety of the aforementioned applications is incorporated herein by reference.

FIELD

This application generally relates to medical devices. In particular, the application relates to devices and methods for endoscopic surgery, e.g., for endoscopic tunnel or pulley release surgery.

BACKGROUND

Endoscopic surgery is a minimally invasive surgical procedure that is performed through small incisions or natural body openings. An endoscopic procedure typically involves use of specialized devices and remote-control manipulation of instruments with indirect observation of the surgical field through an endoscope or similar device. Comparing to open surgery, endoscopic surgery may result in shorter hospital stays, or allow outpatient treatment.

Trigger finger is characterized by catching, snapping or locking of the involved finger flexor tendon, associated with dysfunction and pain. Localized inflammation or nodular swelling of said flexor tendon causes a disparity in size between the flexor tendon and the surrounding retinacular pulley system, most commonly at the level of the first annular (A1) pulley. When the subject extends the involved finger, the tendon will "catch" on the pulley, followed by an abrupt popping of the tendon through the pulley. This results in a difficulty flexing or extending the finger and the "triggering" phenomenon. Typically, a first course of treatment for trigger finger is corticosteroid injections into the tendon sheath to reduce inflammation. When corticosteroid injection is not or no longer effective, surgical division of the A1 pulley is indicated.

Carpal tunnel syndrome is an entrapment median neuropathy resulting from compression of the median nerve at the wrist in the carpal tunnel. Symptoms of carpal tunnel syndrome include tingling, numbness, weakness, or pain felt in the fingers supplied by the median nerve or in the palm. Repetitive tasks, force, posture, and vibration have been cited as causative or contributing factors to carpal tunnel syndrome. Palliative treatments for carpal tunnel syndrome include direct corticosteroid injections, splinting, oral corticosteroids and/or behavior modification. Failure of these methods within a reasonable period of time, and/or the presence of other contributing factors, indicates a need for surgical division of the carpal tunnel.

Other conditions involving the compression of a nerve by a ligament pulley or tunnel include Guyon's tunnel (or canal) syndrome, which is a compression of the ulnar nerve as it passes through Guyon's tunnel at the wrist; cubital tunnel syndrome, which is a compression of the ulnar nerve as it passes through the cubital tunnel at the elbow; radial tunnel syndrome, which is a compression of the radial nerve as it travels from the brachial plexus to the wrist and hand; and pronater teres syndrome, which is a compression neuropathy of the median nerve in the region of the elbow.

Conventional surgical techniques and equipment for pulley or tunnel release require a fairly large incision over the pulley or tunnel and spreading of the incision to allow viewing and instrument access. These techniques can require a longer period of recovery than endoscopic methods and have greater levels of post-operative pain due to the incision size and level of manipulation during the procedure.

Typically, endoscopic surgery has involved a number of steps and separate devices for performing pulley or tunnel division. After making an incision and opening a path to the pulley or tunnel using a blunt instrument, a cannula is inserted into the path. Briefly, in order to smoothly insert the cannula, the central lumen of the cannula must be filled with a device, such as an obturator. The obturator is then removed and an endoscope, or arthroscope, is inserted into the cannula to view the pulley or tunnel. The endoscope is then withdrawn from the cannula, a knife is either advanced into the cannula for division or a specialized knife assembly is affixed to the endoscope and the knife/endoscope assembly is advanced into the cannula for division. The present application fulfills a need in the art for a compact device for uniportal endoscopic pulley or tunnel release surgery that eliminates the need for a separate device, such as an obturator, for filling the cannula during insertion and eliminates the need to remove the endoscope in order to insert a blade or blade assembly.

SUMMARY

One aspect of the present application relates to an endoscopic surgical device, comprising: (a) a housing having a proximate end and a distal end; (b) a slotted clear cannula attached to said distal end of said housing, said slotted clear cannula comprises a cannula body having a proximate end and a distal end, and a slot extending from said proximate end of said cannula to the proximity of said distal end of said cannula; (c) a revolver assembly located within said housing, comprising: a slide lock having a proximate end, a distal end and two notches at said distal end; a scraper; a blade assembly; and a circular revolver body comprising a selector switch; wherein said scraper and said blade reside at said two notches of said slide lock in a pre-deployment position and wherein said selector switch allows selection of said scraper or said blade for deployment; and (d) a tube assembly having a proximate end and a distal end, said distal end of said tube assembly is located within said housing and extends through said revolver, said tube assembly is capable of entering said slotted clear cannula from said proximate end of said clear cannula.

Another aspect of the present invention relates to an endoscopic surgical kit, comprising an endoscope and an endoscopic surgical device, comprising: (a) a housing having a proximate end and a distal end; (b) a slotted clear cannula attached to said distal end of said housing, said slotted clear cannula comprises a cannula body having a proximate end and a distal end, and a slot extending from said proximate end of said cannula to the proximity of said distal end of said cannula; (c) a revolver assembly located within said housing, comprising: a slide lock having a proximate end, a distal end and two notches at said distal end; a scraper; a blade assembly; and a circular revolver body comprising a selector switch; wherein said scraper and said blade reside at said two notches of said slide lock in a pre-deployment position and wherein said selector switch allows selection of said scraper or said blade for deployment; and (d) a tube assembly having a proximate end and a distal end, said distal end of said tube assembly is located within said housing and extends through said revolver, said tube assembly is capable of entering said slotted clear cannula from said proximate end of said clear cannula.

Another aspect of the present invention relates to a method for a performing a uniportal endoscopic surgical procedure on a target tissue using an endoscopic surgical device, comprising: (a) a housing having a proximate end and a distal end; (b) a slotted clear cannula attached to said distal end of said housing, said slotted clear cannula comprises a cannula body having a proximate end and a distal end, and a slot extending from said proximate end of said cannula to the proximity of said distal end of said cannula; (c) a revolver assembly located within said housing, comprising: a slide lock having a proximate end, a distal end and two notches at said distal end; a scraper; a blade assembly; and a circular revolver body comprising a selector switch; wherein said scraper and said blade reside at said two notches of said slide lock in a pre-deployment position and wherein said selector switch allows selection of said scraper or said blade for deployment; and (d) a tube assembly having a proximate end and a distal end, said distal end of said tube assembly is located within said housing and extends through said revolver, said tube assembly is capable of entering said slotted clear cannula from said proximate end of said clear cannula, comprising: establishing an entry portal in said subject, inserting into said entry portal said cannula of said endoscopic surgical device; extending said cannula through said entry portal to said target tissue; advancing an endoscope into said cannula visualize a target tissue; and advancing said blade into said cannula until a desired cut is made on said target tissue.

BRIEF DESCRIPTION OF THE DRAWINGS

The present invention can be better understood by reference to the following drawings. The drawings are merely exemplary to illustrate certain features that may be used singularly or in combination with other features and the present invention should not be limited to the embodiments shown.

FIGS. 11A-E show perspective and cross-sectional views of the cannula element of the embodiment depicted in FIG. 9.

FIGS. 12A-F show perspective and cross-sectional views of the top shell of the housing of the embodiment depicted in FIG. 9.

FIGS. 16A-E show perspective and cross-sectional views of the rotary clip element of the embodiment depicted in FIG. 9.

FIGS. 17A-D show perspective views of the tube assembly element of the embodiment depicted in FIG. 9.

FIGS. 18A-C show perspective views of the blade tool element of the embodiment depicted in FIG. 9.

FIGS. 19A-E show perspective and cross-sectional views of the blade of FIGS. 18A-C.

DETAILED DESCRIPTION

Figure 1:
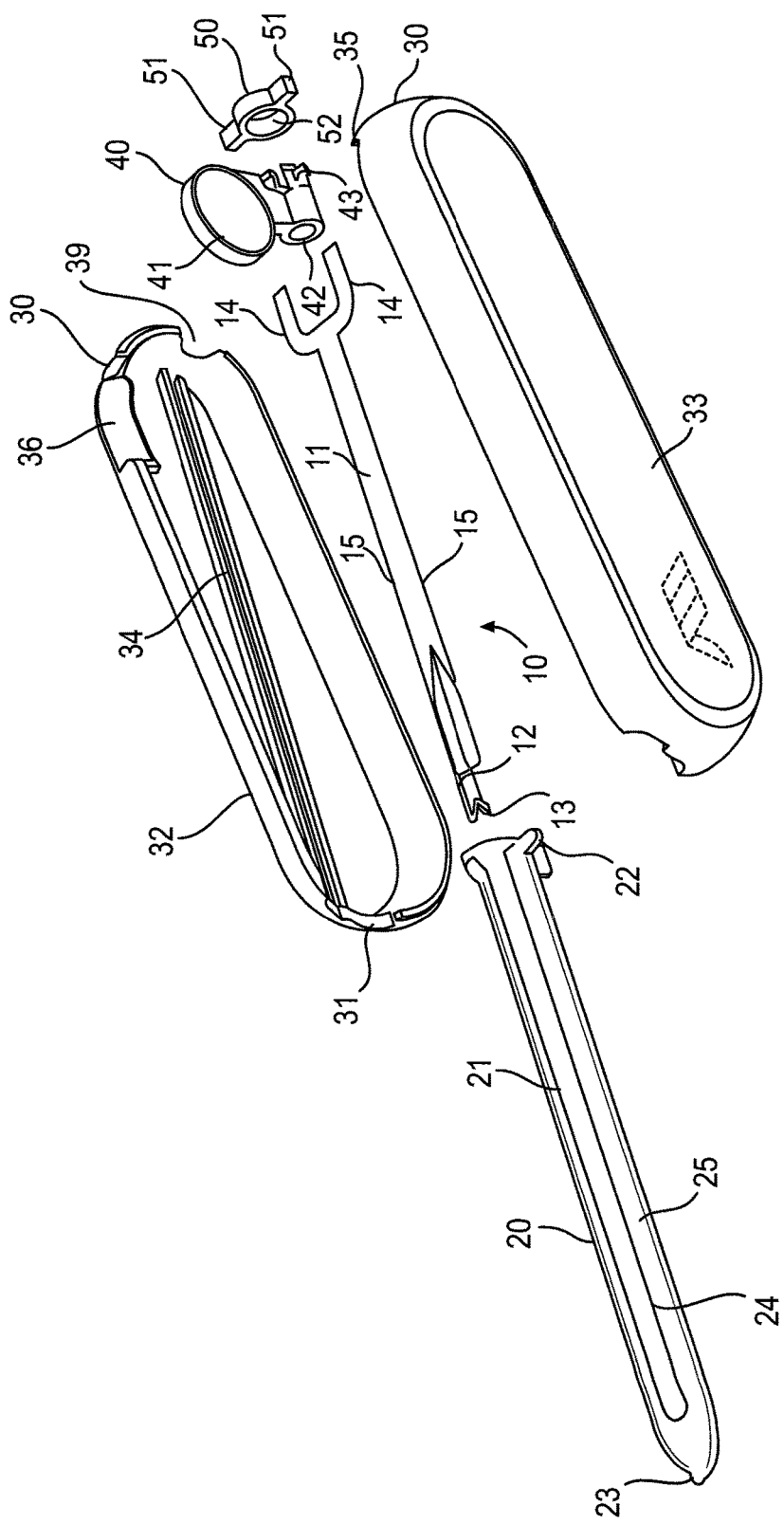
FIG. 1 is an exploded view of one embodiment of the device of the present application.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

This description is intended to be read in connection with the accompanying drawings, which are to be considered part of the entire written description of this application. The drawing figures are not necessarily to scale and certain features of the application may be shown exaggerated in scale or in somewhat schematic form in the interest of clarity and conciseness. In the description, relative terms such as "front," "back," "up," "down," "top," "bottom," "upper," "lower," "distal," and "proximate" as well as derivatives thereof, should be construed to refer to the orientation as then described or as shown in the drawing figure under discussion. These relative terms are for convenience of description and normally are not intended to require a particular orientation. Terms concerning attachments, coupling and the like, such as "connected," "mounted," and "attached," refer to a relationship wherein structures are secured or attached to one another either directly or indirectly through intervening structures, as well as both movable or rigid attachments or relationships, unless expressly described otherwise.

The term "trigger finger," as used herein, also refers to "trigger digit," "trigger thumb," and "stenosing tendovaginitis."

As used herein, the terms "horizontal" and "vertical," and derivatives of those terms, are used in respect to their relationship to the plane defined by the slot in the cannula of the present application. "Vertical" refers to the plane that can, for example, pass through the slot of the cannula and bisect the cannula into two equal halves, while "horizontal" refers to a plane that is perpendicular to the vertical plane. The horizontal plane may be a level plane with respect to the length of the cannula or housing of the device, or may be at an angle to that level plane, allowing some upward or downward movement of elements moving along the horizontal plane with respect to the level plane.

The present application describes a compact device for performing endoscopic surgical procedures, comprising a clear cannula that is attached to a housing. The cannula has a closed distal end, allowing the cannula to be inserted through a portal (such as an incision) without the use of a cannula filling instrument, such as an obturator. The housing further comprises a blade that extends into the cannula, and a paddle for pushing the blade. In some embodiments, the housing further comprises a ring that secures the paddle to the housing, but allows the paddle to rotate side-to-side. The present assembly provides a convenient means for performing endoscopic surgical procedures with the elimination of the steps of inserting an obturator into the cannula for introducing the cannula into a portal, removing the obturator from the cannula, and removing an endoscope from the cannula so that a blade can be inserted and advanced into the cannula. The preassembled nature of the device also provides convenience for the practitioner in that the cannula and blade are available in a single package that requires no further assembly and can be used easily in an office setting without the need for some traditional endoscopic equipment that may be too expensive or cumbersome to use outside of a hospital. Additionally, the present device also can be easily transported and used in remote settings, such as by emergency medical personnel, first responders or military medical personnel.

The use of the present device is exemplified in this application for, but not limited to, endoscopic surgical division of a pulley or tunnel. Some other non-limiting uses for the present device include, for example, other divisions or partial separation of a tendon or ligament, cutting, dividing, separating or making an incision in connective tissue, muscle, cartilage, membranes, skin, other body tissues or organs or any other use of the device that can be envisioned or carried out by the practitioner. As used herein, the term "practitioner" refers to one of skill in the art or any other user of the present device.

Endoscopic surgical procedures that can be performed with a device of the present application include, but are not limited to, carpal tunnel release, Guyon's tunnel (or canal) release, cubital tunnel release, plantar fascia release, lateral release for patella realignment, release of radial tunnel, release of pronatar teres, release of trigger finger, release of lacertus fibrosus, release of the extensor tendons for lateral epicondylitis, release of medial epicondylitis, release of the posterior and other compartments of the leg, forearm fascia release for fascial compartment syndrome, release of fascial compartments in the upper or lower extremities, relieving the compression of a nerve by a ligament pulley or tunnel, and releasing the travel of a ligament through a ligament pulley or tunnel.

One aspect of the present application relates to an endoscopic surgical device, comprising: (a) a housing having a proximate end and a distal end; (b) a slotted clear cannula attached to said distal end of said housing, said slotted clear cannula comprises a cannula body having a proximate end and a distal end, and a slot extending from said proximate end of said cannula to the proximity of said distal end of said cannula; (c) a revolver assembly located within said housing, comprising: a slide lock having a proximate end, a distal end and two notches at said distal end; a scraper; a blade assembly; and a circular revolver body comprising a selector switch; wherein said scraper and said blade reside at said two notches of said slide lock in a pre-deployment position and wherein said selector switch allows selection of said scraper or said blade for deployment; and (d) a tube assembly having a proximate end and a distal end, said distal end of said tube assembly is located within said housing and extends through said revolver, said tube assembly is capable of entering said slotted clear cannula from said proximate end of said clear cannula.

In one embodiment, the end of the slotted clear cannula distal to the housing is closed. In a further embodiment, the closed end of the cannula is tapered.

In another embodiment of the endoscopic surgical device, said housing further comprises a stabilizing ring that mounts into said proximate end of said housing.

In another embodiment, the endoscopic surgical device further comprises a rotary clip that prevents said scraper and said blade from sliding in undeployed positions. In a further embodiment, said rotary clip comprises a tab that engages with an inside surface of said housing and an opening that allows deployment of said scraper or said blade.

In another embodiment of the endoscopic surgical device, said circular body of said revolver comprises a hooked tab that engages with said slide lock. In a further embodiment, said circular body of said revolver further comprises a set of upper tabs and a set of lower tabs, wherein said upper tabs and said lower tabs extend inwardly from an interior surface of said circular body.

In still another embodiment of the endoscopic surgical device, said slide lock comprises a tab located between said two notches at said distal end. In a further embodiment, said slide lock further comprises one or more retaining tabs that hold a rotary clip.

In yet another embodiment of the endoscopic surgical device, said slide lock comprises a pair of wings that engage with said revolver. In a further embodiment, said slide lock further comprises a disc at said proximate end of said slide lock.

In yet still another embodiment of the endoscopic surgical device, said tube assembly comprises a tool selector at said distal end of said tube assembly. In a further embodiment, said tool selector is welded onto said tube assembly. In another further embodiment, said tube assembly further comprises a tube stop at said proximate end of said tube assembly.

In still another embodiment of the endoscopic surgical device, said blade assembly comprises a pusher base and a cutting blade. In a further embodiment, said pusher base comprises a notch that is capable of engaging with a tool selector on said tube assembly. In another further embodiment, said cutting blade comprises a tab that embeds into said pusher base. In still another further embodiment, said cutting blade comprises an upper cutting surface that forms an upper angle with a bottom surface of said cutting blade. In a further embodiment, said upper angle is between about 30 and about 45 degrees. In yet another further embodiment, said cutting blade further comprises a lower cutting surface that forms a lower angle with a bottom surface of said cutting blade. In a further embodiment, said lower angle is between about 45 and about 65 degrees.

In yet another embodiment of the endoscopic surgical device, said scraper comprises a notch that is capable of engaging with a tool selector on said tube assembly.

Another aspect of the present invention relates to an endoscopic surgical kit, comprising an endoscope and an endoscopic surgical device, comprising: (a) a housing having a proximate end and a distal end; (b) a slotted clear cannula attached to said distal end of said housing, said slotted clear cannula comprises a cannula body having a proximate end and a distal end, and a slot extending from said proximate end of said cannula to the proximity of said distal end of said cannula; (c) a revolver assembly located within said housing, comprising: a slide lock having a proximate end, a distal end and two notches at said distal end; a scraper; a blade assembly; and a circular revolver body comprising a selector switch; wherein said scraper and said blade reside at said two notches of said slide lock in a pre-deployment position and wherein said selector switch allows selection of said scraper or said blade for deployment; and (d) a tube assembly having a proximate end and a distal end, said distal end of said tube assembly is located within said housing and extends through said revolver, said tube assembly is capable of entering said slotted clear cannula from said proximate end of said clear cannula.

In another embodiment, the kit further comprises a scalpel.

In yet another embodiment, the kit further comprises a blunt instrument for tissue separation. In a still further embodiment, the blunt instrument is an elevator.

Another aspect of the present invention relates to a method for a performing a uniportal endoscopic surgical procedure on a target tissue using an endoscopic surgical device, comprising: (a) a housing having a proximate end and a distal end; (b) a slotted clear cannula attached to said distal end of said housing, said slotted clear cannula comprises a cannula body having a proximate end and a distal end, and a slot extending from said proximate end of said cannula to the proximity of said distal end of said cannula; (c) a revolver assembly located within said housing, comprising: a slide lock having a proximate end, a distal end and two notches at said distal end; a scraper; a blade assembly; and a circular revolver body comprising a selector switch; wherein said scraper and said blade reside at said two notches of said slide lock in a pre-deployment position and wherein said selector switch allows selection of said scraper or said blade for deployment; and (d) a tube assembly having a proximate end and a distal end, said distal end of said tube assembly is located within said housing and extends through said revolver, said tube assembly is capable of entering said slotted clear cannula from said proximate end of said clear cannula, comprising: establishing an entry portal in said subject, inserting into said entry portal said cannula of said endoscopic surgical device; extending said cannula through said entry portal to said target tissue; advancing an endoscope into said cannula visualize a target tissue; and advancing said blade into said cannula until a desired cut is made on said target tissue.

In one embodiment, the establishing an entry portal comprises making an incision.

In one embodiment, an endoscope is inserted through the housing and into the cannula to view the target tissue and the surrounding tissues, assuring that the slot of the cannula is in proper orientation to the target tissue.

In a further embodiment, the knife is advanced through the cannula so that the blade moves in contact with the target tissue through the slot, operatively engaging the target tissue with the blade. In a still further embodiment, the desired cut is division of the target tissue.

In a particular embodiment, the method further comprises advancing said scraper into said cannula to remove tenosynovium.

In another particular embodiment of the method, the uniportal endoscopic surgical procedure is selected from the group consisting of trigger finger release, carpal tunnel release, cubital tunnel release, plantar fascia release, lateral release for patella realignment, release of the extensor tendons, release of the posterior or other compartments of the leg, and forearm fascial release.

In still another particular embodiment of the method, the target tissue is selected from the group consisting of the A1 pulley, carpal tunnel, cubital tunnel and Guyon's tunnel.

Linear Operated Device

FIG. 1 shows an exemplary device of the present application. The device comprises a blade 10, a slotted clear cannula 20, and a housing 30. The device may further include a pusher paddle 40, and may still further include a retainer ring 50.

The blade 10 comprises a horizontally-oriented pushing component 11 and a vertically-oriented cutting component 12. The cutting component 12 further comprises a sharpened cutting surface 13 at the forward end, which is the end of the blade most proximal to the cannula 20 of the device. The cutting surface 13 may be single-beveled or double-beveled.

In some embodiments, the cutting surface 13 of the blade is a single cutting surface. In some further embodiments, that single cutting surface is angled downward such that the upper end of the cutting surface is forward of the lower end of the cutting surface. In other further embodiments, that single cutting surface has a concave curve and is semicircular or crescent shaped.

In other embodiments, the cutting surface 13 of the cutting component 12 is divided into an upper cutting surface and a lower cutting surface that are at an angle to one another and meet at a central crotch.

The design of the present blade 10 is such that it is usable in endoscopic surgery in a manner that allows the practitioner to extend the blade 10 through the cannula to the target tissue without damage to surrounding tissue and/or organs. The cutting component 12 of blade 10 is made from materials commonly used for surgical blades or scalpels, such materials include, but are not limited to, hardened and tempered steel, stainless steel, high carbon steel, titanium, alloys and ceramic.

In particular embodiments, the cutting component 12 of the blade 10 is made from stainless steel. In a further embodiment, the stainless steel is martensitic stainless steel. An exemplary martensitic stainless steel is Bohler-Uddeholm AEB-L martensitic stainless steel. In a still further embodiment, the martensitic stainless steel is heat-treated. In another further embodiment, the stainless steel is 440 A stainless steel. In a particular embodiment, the cutting component 12 of the blade 10 is made from Hitachi GIN-5 SST-MODIFIED 440-A stainless steel. The cutting component 12 of the blade 10 is optionally flash electropolished. The cutting edges are machine finished and must be sharp. In a particular embodiment, the steel of the cutting component 12 of the blade 10 is heat-treated to Rockwell C hardness of about 50-72. In a more particular embodiment, the steel of the cutting component 12 of the blade 10 is heat-treated to Rockwell C hardness of 58-64.

In particular embodiments, the entire blade 10 is cut from a single sheet of, or is cast from, a material commonly used for surgical blades or scalpels. The cutting component 12 is then bent into a vertical orientation that is perpendicular to the horizontal orientation of the pushing component 11. In some embodiments, the bevel(s) of the cutting surface 13 are ground prior to bending. In other embodiments, the bevel(s) of the cutting surface 13 are ground after bending.

In other embodiments, the pushing component 11 and cutting component 12 of the blade 10 are fabricated separately (by cutting or casting) and affixed to one another in their respective proper orientations. In some further embodiments, the pushing component 11 and cutting component 12 are fabricated from the same material. In other further embodiments, the pushing component 11 and cutting component 12 are fabricated from different materials, but at least the cutting component 12 is fabricated from a material commonly used for surgical blades or scalpels. In such a case, the pushing component 11 of the blade 10 may be fabricated from any suitable material providing adequate strength and rigidity for pushing the cutting component including, but not limited to, plastics, polycarbonate, hardened and tempered steel, stainless steel, high carbon steel, titanium, alloys and ceramic. Affixing of the cutting component 12 to the pushing component 11 may be accomplished by any means known in the art, such as the use of a suitable adhesive or by welding, including laser welding. In a particular embodiment, the strength of the bond between the pushing component 11 and the cutting component 12 is tested by applying torque to the unit, for example about 10 in-lbs of torque.

In particular embodiments, the blade 10 further comprises tabs 14 at the end of the pushing component 11 distal to the cutting component 12. In some embodiments, the tabs 14 extend outward to the sides of the blade 10 in the same horizontal plane as the pushing component 11, although in some embodiments, the tabs 14 may also be at an angle to that horizontal plane, as appropriate for the application. As used herein, the term "tabs" refers to either a single tab structure, two tab structures, or any other multiple as appropriate.

The tabs 14 are slidably engaged with the case or housing 30 in a manner to be further described below.

The cannula 20 is made of a clear plastic material so that the entirety of the surrounding tissue can be viewed with an endoscope. The cannula 20 is slotted along its top, with the slot 21 being contiguous with the open end 22 that is proximal to the housing 30. in some embodiments, the distal end 23 of the cannula 20 is closed, such that the cannula 20 can be inserted into a channel made through body tissue without the use of an obturator. In particular embodiments, the closed distal end 23 of the cannula is tapered, but is sufficiently blunted such that it does not damage bodily tissues as it is advanced though an incision and channel through bodily tissue, or through a natural body opening.

The cannula 20 engages with the blade 10 of the device such that the cutting component 12 inserts into and is slidably engaged with the slot 21.

In some embodiments, the cannula 20 further internally comprises horizontal blade guidance tracks 24 perpendicular to the plane of and below the slot 21. The sides 15 of the pushing component 11 of the blade 10 slidably engage with the horizontal blade guidance tracks 24, in order to allow the accurate advancement of the cutting component 12 of the blade 10 through the slot 21. In some further embodiments, the height of the horizontal blade guidance tracks 24 is level with respect to the distance from the slot 21, such that the distance the cutting surface 13 protrudes through the slot 21 is the same over the entire course of travel from the proximal end 22 of the cannula 20 to the distal end 23 of the cannula 20. In other further embodiments, the height of the horizontal blade guidance tracks 24 is at an angle with respect to the distance from the slot 21, such that the distance the cutting surface 13 protrudes through the slot 21 is lower at or near the proximal end 22 of the cannula 20 and higher at or near the distal end 23 of the cannula 20.

In some embodiments, the cannula 20 further comprises a channel 25 for the slidable insertion a viewing device, such as an endoscope. In some embodiments, the channel 25 is located below the horizontal blade guidance tracks 24. In some embodiments, the channel 25 and the horizontal blade guidance tracks 24 form a single contiguous lumen that is also contiguous with the slot 21. In other embodiments, there is a layer of material molded as part of the cannula 20 between the channel 25 and the horizontal blade guidance tracks 24, such that the lumen of the channel 25 is physically separate from the lumen contiguous with the slot 21 and comprising the horizontal blade guidance tracks 24.

In some embodiments, the proximal end 22 of the cannula 20 is adapted to engage with a connection point 31 on the front end of the housing 30. The attachment can be by any means known in the art, such as, but not limited to, adhesives, tabs, welds, laser welds, locking mechanism, twist-lock, or friction fitting. In order to provide a stable platform for endoscopic surgical procedures using the device, the attachment of the cannula 20 to the housing 30 is such that, when assembled, the cannula 20 cannot move in relation to the housing 30.

In some embodiments, the housing 30 of the device comprises two halves 32, 33 that mate to one another to form a single housing 30. In some embodiments, the housing 30 may be formed as a single piece or comprise three or more pieces.

The interior of the housing 30 comprises a guidance slot 34 on each side of the housing such that the two guidance slots 34 are horizontally opposed to one another. The tabs 14 of the blade 10 are slidably engaged with the horizontally opposed guidance slots 34. In some embodiments, the height of the horizontally opposed guidance slots 34 is parallel to with respect to a horizontal plane that would bisect the cannula 20 into two equal halves. In other embodiments, the height of the horizontally opposed guidance slots 34 is at an angle with respect to a horizontal plane that would bisect the cannula 20 into two equal halves, such that the end of the horizontally opposed guidance slots 34 distal to the cannula 20 is lower in the device with respect to the end of the horizontally opposed guidance slots 34 proximal to the cannula 20.

When the tabs 14 are drawn back in the horizontally opposed guidance slots 34, the cutting component 12 is contained within the proximate end 22 of the slot 21 of the cannula 20 and the cutting surface 13 is not protruded outside the device. As the tabs 14 are advanced in the horizontally opposed guidance slots 34 toward the connection point 31 with the cannula 20, the cutting component 12 slides in the proximate direction of the slot 21 of the cannula 20 and moves the cutting surface 13 toward the proximate end 23 of the cannula 20.

In some embodiments, the device comprises a paddle 40 that contacts the blade 10 behind or between the tabs 14. The paddle 40 comprises a grip area 41 that protrudes out of the housing 30 through a slot 35. The blade 10 is slidably advanced along the horizontally opposed guidance slots 34 by advancing the paddle 40 towards the cannula 20 through the slot 35, causing the contact area 42 of the paddle 40 to push against the pushing component 11 of the blade 10.

In some embodiments, the paddle 40 comprises at least one arm that extends forward of the tabs 14 that allows the paddle 40 to capture the tab 14 and pull the blade 10 back to a withdrawn position following completion of an endoscopic surgical procedure.

In some embodiments, the paddle 40 is secured in the device by a retaining ring 50. The retaining ring 50 comprises wings 51 that slidably interact with the horizontally opposed guidance slots 34 of the housing 30. The retaining ring 50 further comprises an attachment ring 52 that connects to the connection region 43 of the paddle 40. The connection region 43 of the paddle 40 may comprise any means known in the art for connecting the paddle 40 to the retaining ring 50. For example, the connection region 43 may comprise tabs that extend through and entrap the attachment ring 52. In some embodiments, the connection between the connection region 43 and the attachment ring 52 allows the paddle 40 to rotate side-to-side in relation to the retaining ring and the blade 10.

In some embodiments, the paddle 40 can be retained, parked or locked in a position fully distal to the cannula 20 by rotating the grip area 41 of the paddle 40 into, for example, a notch 36 in the housing 30.

In some embodiments, the housing 30 further comprises an opening 39 at the end distal to the cannula 20 through which an endoscope can be inserted. The endoscope is fed through the opening 39 and under the blade 10 to be inserted into the channel 25 of the catheter 20. this allows direct visualization of the surgical site and the surrounding tissue before, during and after performing an endoscopic surgical procedure with the present device.

Another aspect of the present application relates to a slotted clear cannula having a closed end such that the cannula can be inserted into an incision or natural body opening and into a passage through body tissue without the use of a device, such as an obturator, filling the lumen of the cannula for insertion. In particular embodiments, the closed end of the cannula is tapered, but is sufficiently blunted such that it does not damage bodily tissues as it is advanced though an incision and channel through bodily tissue, or through a natural body opening. In another particular embodiment, the slot is contiguous with the open end of the cannula opposite the closed end.

Rotationally Operated Devices

Figure 2:
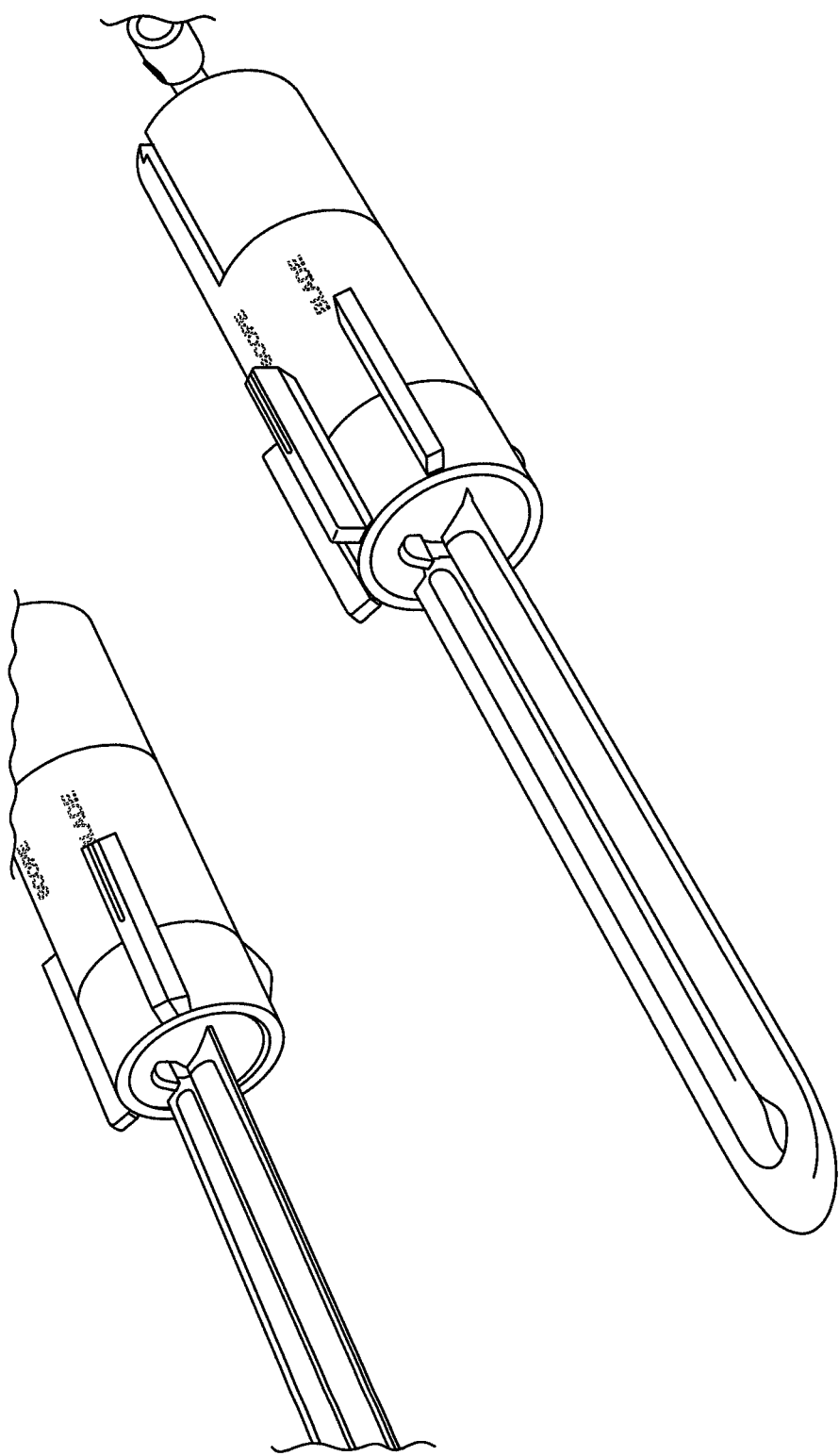
FIG. 2 is a perspective view of another embodiment of the device of the present application.
Figure 3:
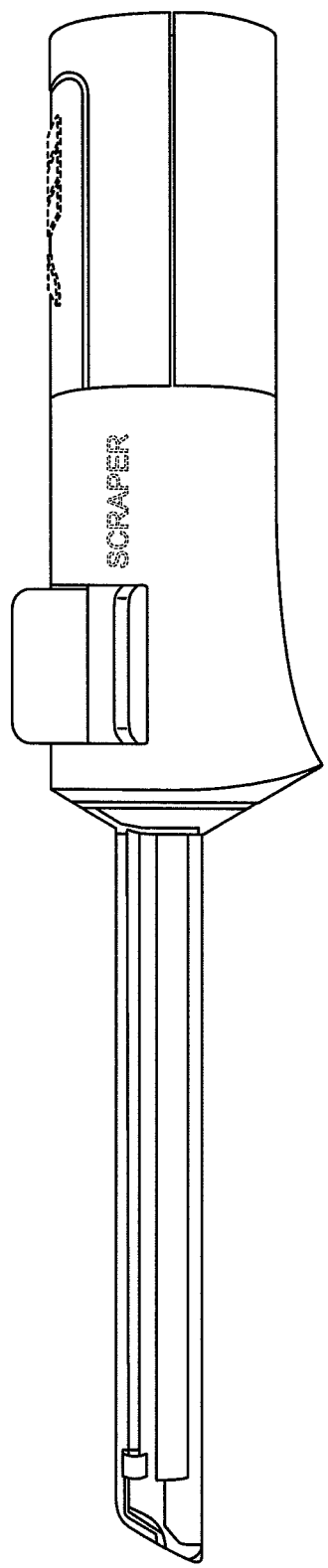
FIG. 3 is a perspective view of another embodiment of the device of the present application.

FIGS. 2 and 3 show embodiments of the present application wherein the device comprises a rotational switch for selecting the tool to advance into the cannula. FIG. 2 shows an embodiment comprising selection positions for advancing the endoscope alone into the cannula and for advancing a blade along the endoscope into the cannula. FIG. 3 shows an alternate embodiment, wherein the device further comprises a selectable scraper that can be advanced along the endoscope into the cannula.

Figure 4:
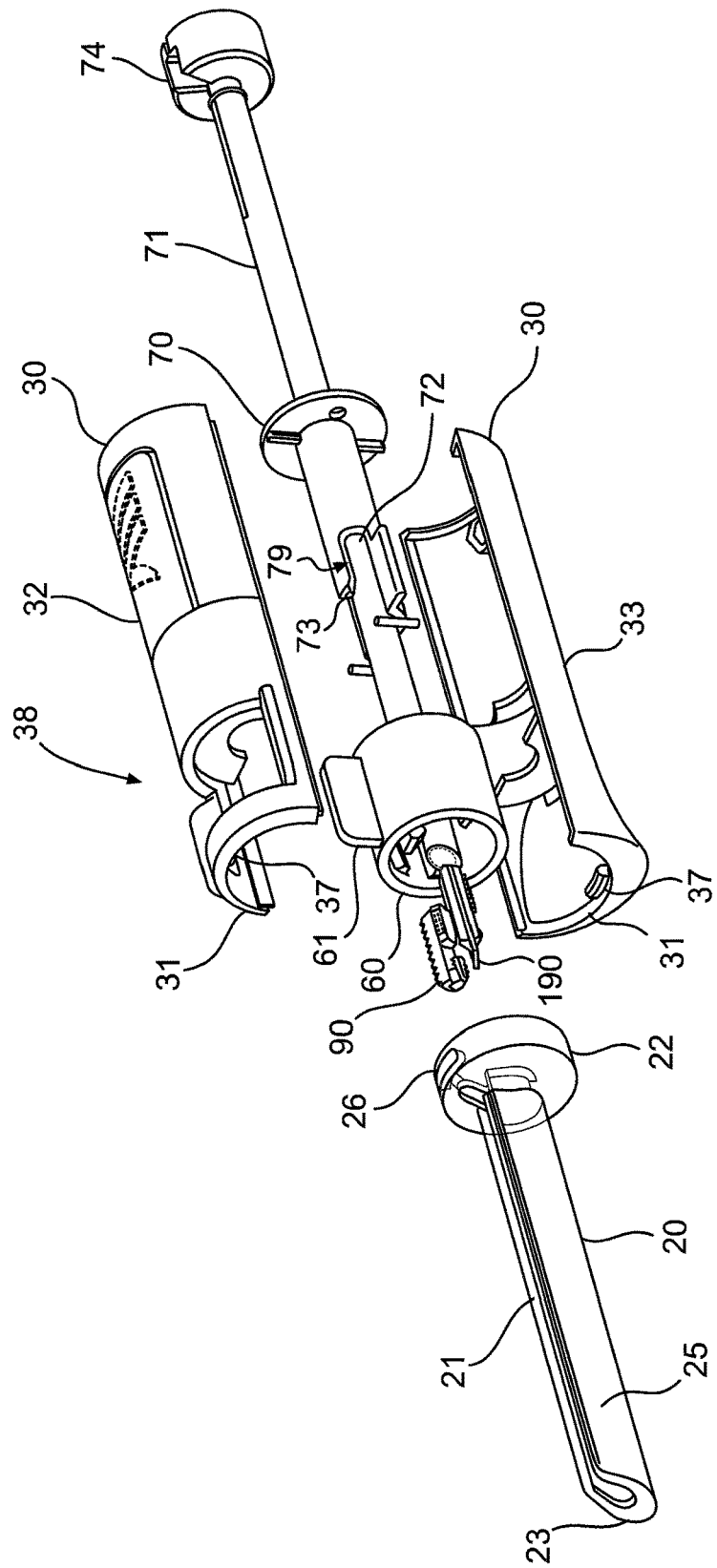
FIG. 4 is an exploded view of the embodiment of the embodiment depicted in FIG. 3.

FIG. 4 depicts an exploded view of the present device of FIG. 3. The housing 30 is cylindrical in shape and is comprised of two halves 32,33. The proximal end 22 of the cannula 20 is adapted to engage with a connection point 31 on the front end of the housing 30. In some embodiments, the proximal end 22 of the cannula 20 comprises depressions 26 that engage with tabs (or pins) 37 at the connection point 31 on the front end of the housing 30. As used herein, the term "depression" is understood to include, but is not limited to, depressions that do not penetrate completely through the material of the cannula, as well as holes or slots that penetrate completely through the material of the cannula.

The housing 30 further includes an opening 38 that can be located in either half 32,33 of the housing. in some embodiments, the opening 38 may span the junction between the halves 32,33 of the housing 30, being located partially in each half. The opening 38 is located adjacent to an internal revolver 60 that comprises a selector switch 61 that protrudes through the opening 38.

Still referring to FIG. 4, the device further comprises an slide lock 70 (or inner sleeve 70) that encircles a guidance tube or tube assembly 71. The slide lock 70 comprises notches 72,73 and a tub 79 separating the notches 72,73, at its distal end that provide pre-deployment resting places for a blade 80 and a scraper 90. The slide lock 70 works in concert with the revolver 60 in order to bring the blade 80 or scraper 90 into the proper orientation for deployment into the slot 21 of the cannula 20. The tube assembly 71 provides a path for deploying an endoscope through the device and into the cannula 20. The tube assembly 71 also provides, at its distal end, a mounting point or tube locator 78 (shown in FIG. 8A) that the blade 80 or scraper 90 is rotated onto for deployment. At the proximate end of the housing, the tube assembly passes through a stabilizer ring 74, which mounts into, and seals, the proximate end of the housing. The tube assembly 71 is advanced along the deployed endoscope into the cannula 20, thereby deploying the blade 80 or scraper 90 into the slot 21 of the cannula 20.

Figure 5:
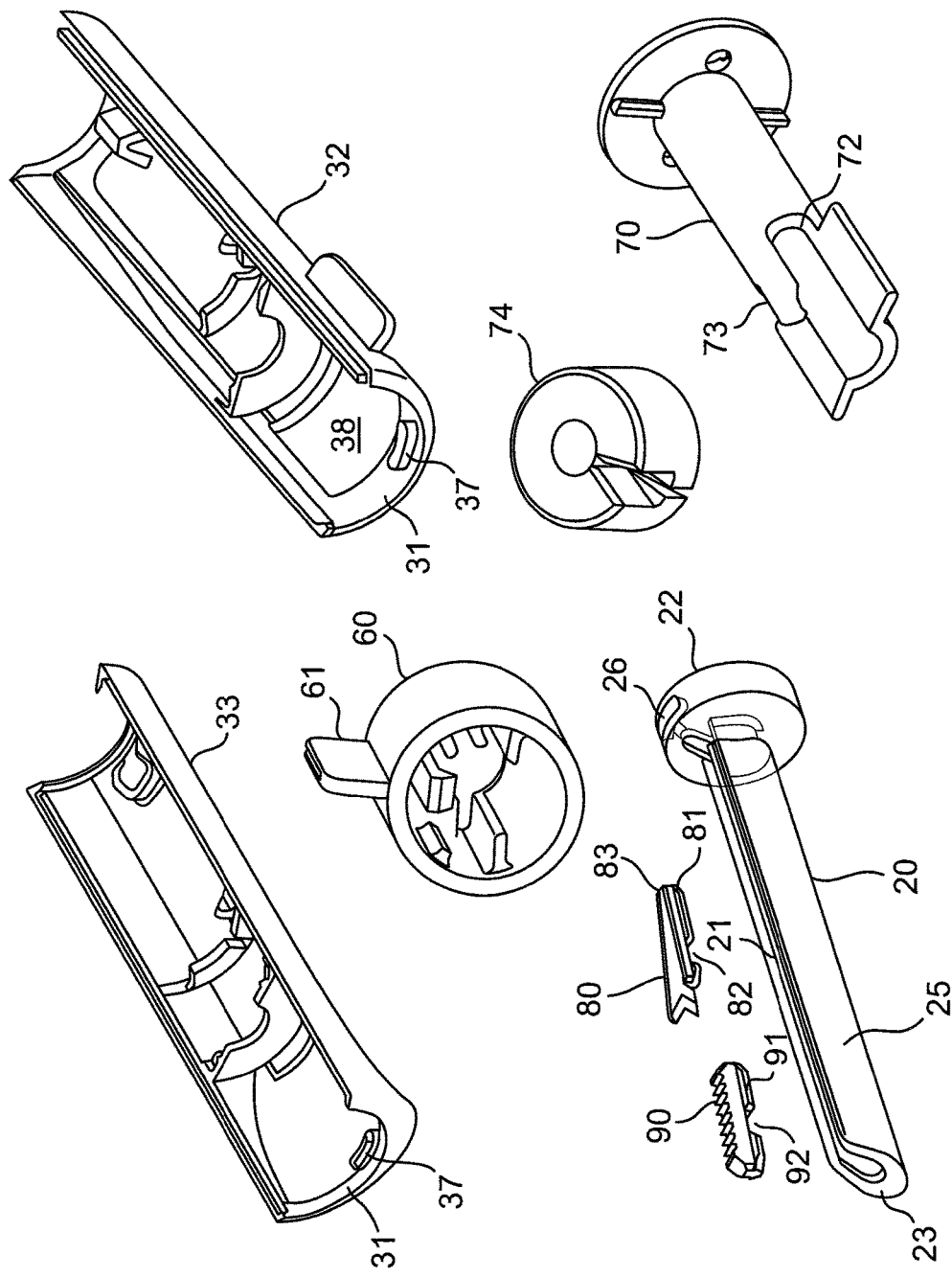
FIG. 5 shows individual components of the embodiment depicted in FIG. 3.

Turning to FIG. 5, a number of components of the device depicted in FIG. 3 are shown separately from one another. It is understood that the individual elements of the device are not limited to the exact configuration depicted in the figures herein. Any design of particular elements of the device that can be envisioned by one of ordinary skill in the art to perform the same function in concert with other elements is included as part of the present disclosure.

Also in FIG. 5, the blade 80 comprises a base 81 that allows the blade 80 to be secure in its pre-deployment notch 72 of the slide lock 70. When the blade 80 is rotated into deployment orientation, the notch 82 in the base 81 engages the mounting point 78 (shown in FIG. 8A) on the distal end of the guidance tube 71. As the blade 80 is distally deployed into the slot 21 of the cannula 20, the base 81 retains the blade 80 in the device by underlapping the sides of the slot 21 within the channel 25 of the cannula 20. Additionally, to prevent any unwanted side-to-side motion of the blade 80 as it is deployed distally through the slot 21 of the cannula 20, in some embodiments the blade further comprises a ridge 83 that fills the slot side-to-side. Additionally, the engagement of the notch 82 with the mounting point 78 allows the blade 80 to be safely retracted back into the housing 30 following usage of the blade 80 for an endoscopic surgical procedure.

Still referring to FIG. 5, the scraper 90 comprises a base 91 that allows the scraper 90 to be secure in its pre-deployment notch 73 of the slide lock 70. When the scraper 90 is rotated into deployment orientation, the notch 92 in the base 91 engages the mounting point 78 (shown in FIG. 8A) on the distal end of the guidance tube 71. As the scraper 90 is distally deployed into the slot 21 of the cannula 20, the base 91 retains the scraper 90 in the device by underlapping the sides of the slot 21 within the channel 25 of the cannula 20. Additionally, the engagement of the notch 92 with the mounting point 78 allows the scraper 90 to be safely retracted back into the housing 30 following usage of the scraper 90 for an endoscopic surgical procedure.

Figure 6:
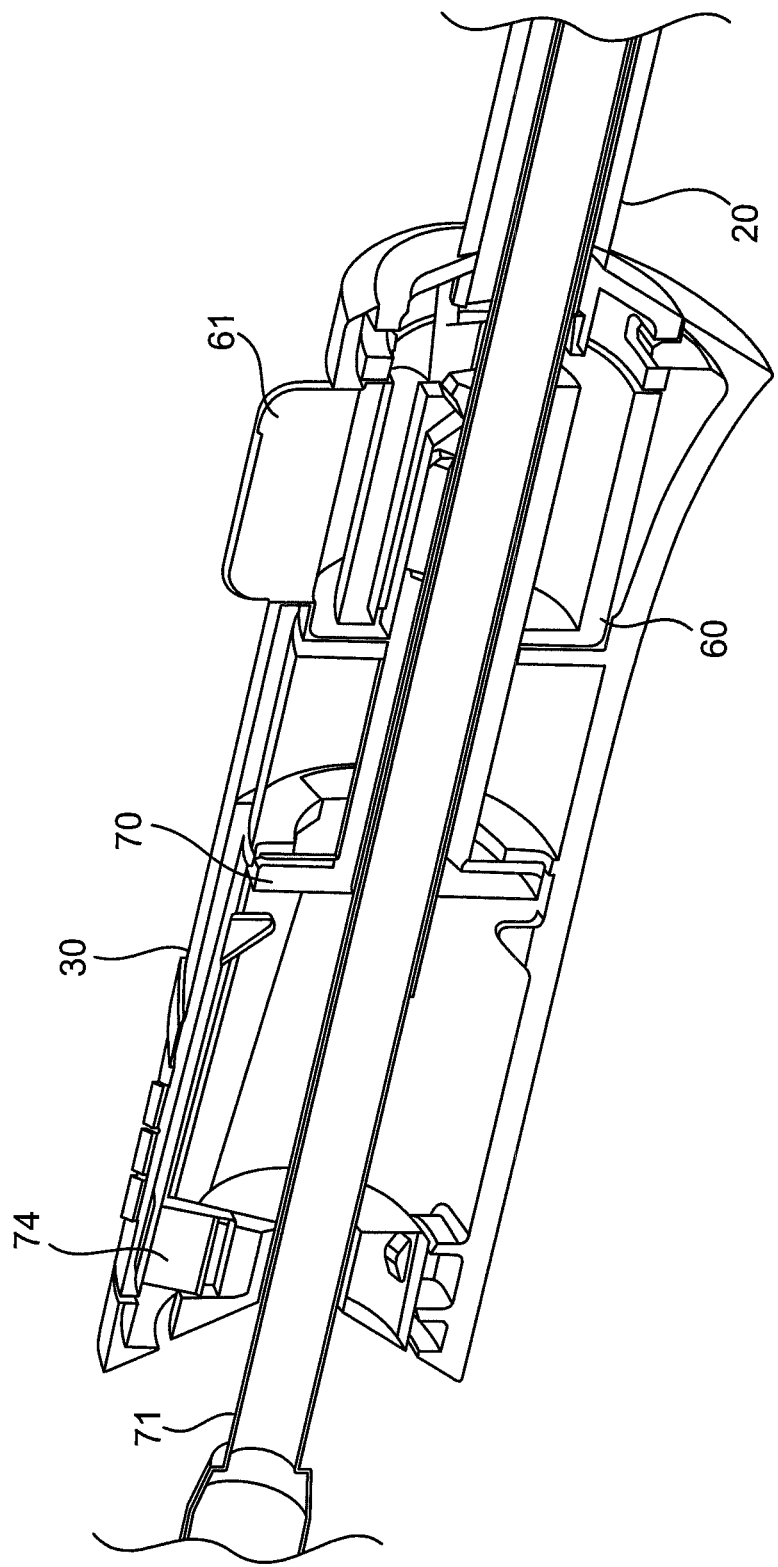
FIG. 6 is a cutaway view of the embodiment of the embodiment depicted in FIG. 3.

Turning to FIG. 6, a cutaway drawing is shown that depicts the passage of the guidance tube or tube assembly 71 through the slide lock 70 and into the cannula 20.

Figure 7:
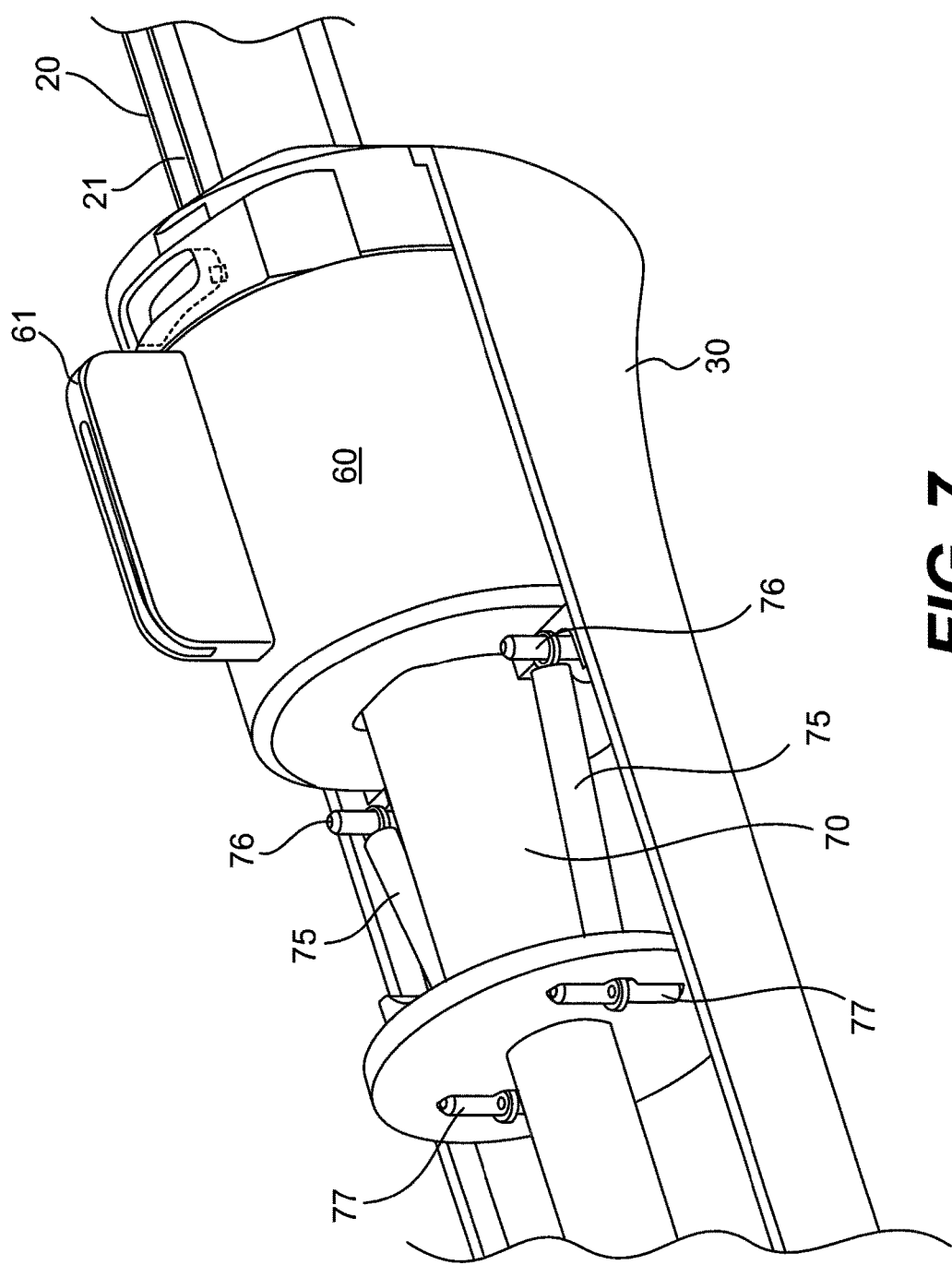
FIG. 7 is an exploded view of individual components of the embodiment depicted in FIG. 3.

FIG. 7 is a cutaway drawing showing an exemplary relationship of the slide lock 70 to the revolver 60 of the device. The slide lock 70 extends into the revolver 60 and the pre-deployment slots 72,73 holding the blade 80 and the scraper 90 are located inside the revolver 60. In an exemplary configuration, springs 75 are attached to pins 76 located on the revolver 60. The springs 75 extend to pins 77 that secure the opposite end of the springs to the slide lock 70. The springs 75 auto center the revolver 60 within the device. Upon rotation of the revolver 60, the springs 75 activate detents for the three modes: 1) deployment of the endoscope, 2) orientation of the scraper 90 in deployment configuration, and 3) orientation of the blade 80 in deployment configuration.

Figure 8C:
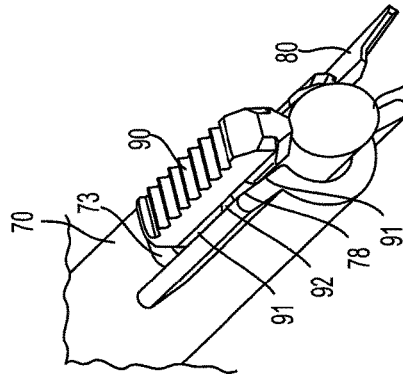
FIGS. 8A-F show the orientation of the internal components in side view (A, C, E) and end view (B, D, F) of the embodiment of FIG. 3 for the advancement of an endoscope alone (A, B), an endoscope with a scraper (C, D) or an endoscope with a blade (E, F).
Figure 8F:
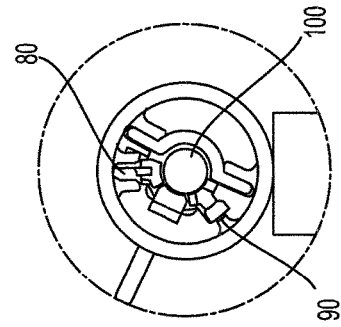
Figure 8B:
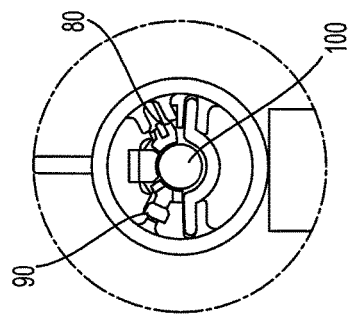
Figure 8E:
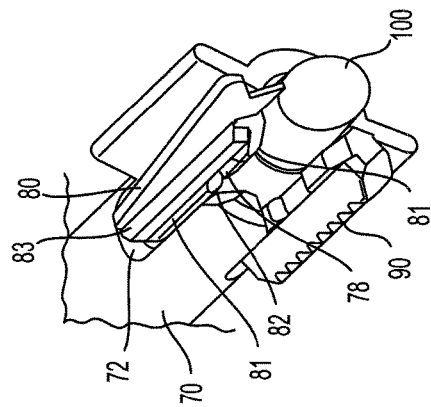
Figure 8A:
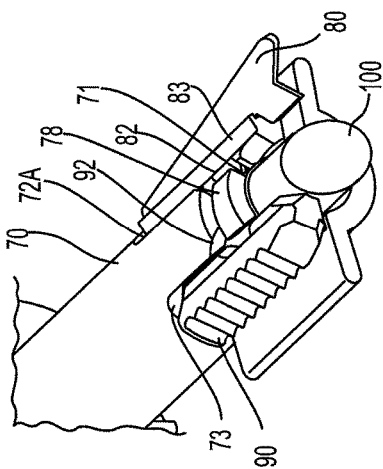
Figure 8D:
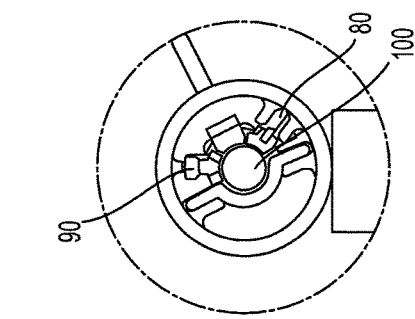

FIGS. 8A-F show the rotation of the slide lock corresponding to the three modes. FIG. 8A, viewing from above, and 8B, viewing from a distal position, are a depiction of the first mode, wherein the an endoscope 100 can be advanced through the guidance tube 71 into the cannula 20, without the deployment of the scraper 90 or the blade 80. The mounting point 78 is not engaged with either the blade 80 or the scraper 90, therefore preventing the deployment of either tool in this mode.

FIG. 8C, viewing from above, and 8D, viewing from a distal position, are a depiction of the second mode, wherein the revolver 60 has been turned to select the scraper 90. the slide lock 70 is rotated in concert with the revolver 60 to bring the scraper 90 into deployment orientation. The slot 92 in the base 91 of the scraper 90 is rotated to engage the mounting point 78 on the guiding tube (hidden). The guiding tube is then pushed distally into the cannula 20 with the scraper 90 protruding through the slot 21. Following use of the scraper 90, the guiding tube is retracted from the cannula 20 and the revolver 60 is returned to the first mode, restoring the scraper to its pre-deployment configuration of FIGS. 8A-B.

FIG. 8E, viewing from above, and 8F, viewing from a distal position, are a depiction of the third mode, wherein the revolver 60 has been turned to select the blade 80. The slide lock 70 is rotated in concert with the revolver 60 to bring the blade 80 into deployment orientation. The slot 82 in the base 81 of the blade 80 is rotated to engage the mounting point 78 on the guiding tube (hidden). The guiding tube is then pushed distally into the cannula 20 with the blade 80 protruding through the slot 21. Following use of the blade 80, the guiding tube is retracted from the cannula 20 and the revolver 60 is returned to the first mode, restoring the blade 80 to its pre-deployment configuration of FIGS. 8A-B.

Figure 9:
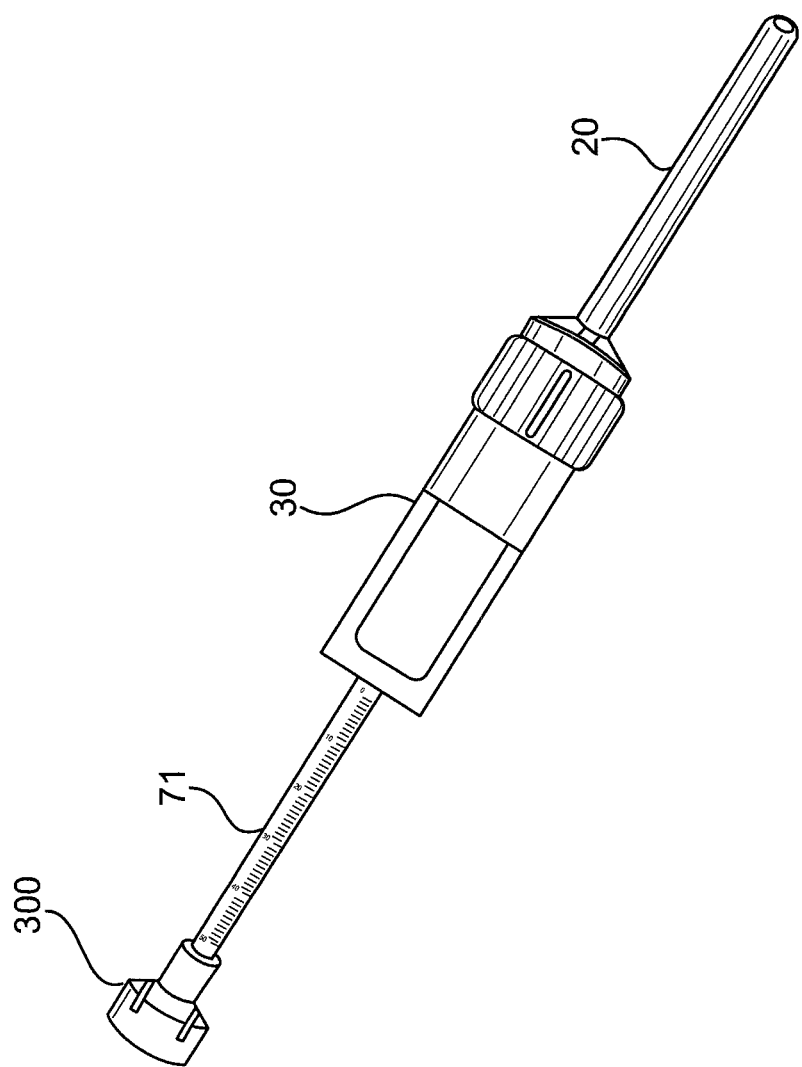
FIG. 9 is a perspective view of another embodiment of the device of the present application.

FIG. 9 is a perspective view from above an embodiment of the device showing, in particular, the cannula 20, housing 30 and tube assembly 71 as they appear in the assembled device prior to deployment of the tube assembly 71 into the cannula 20 with the scraper tool or blade assembly.

Figure 10:
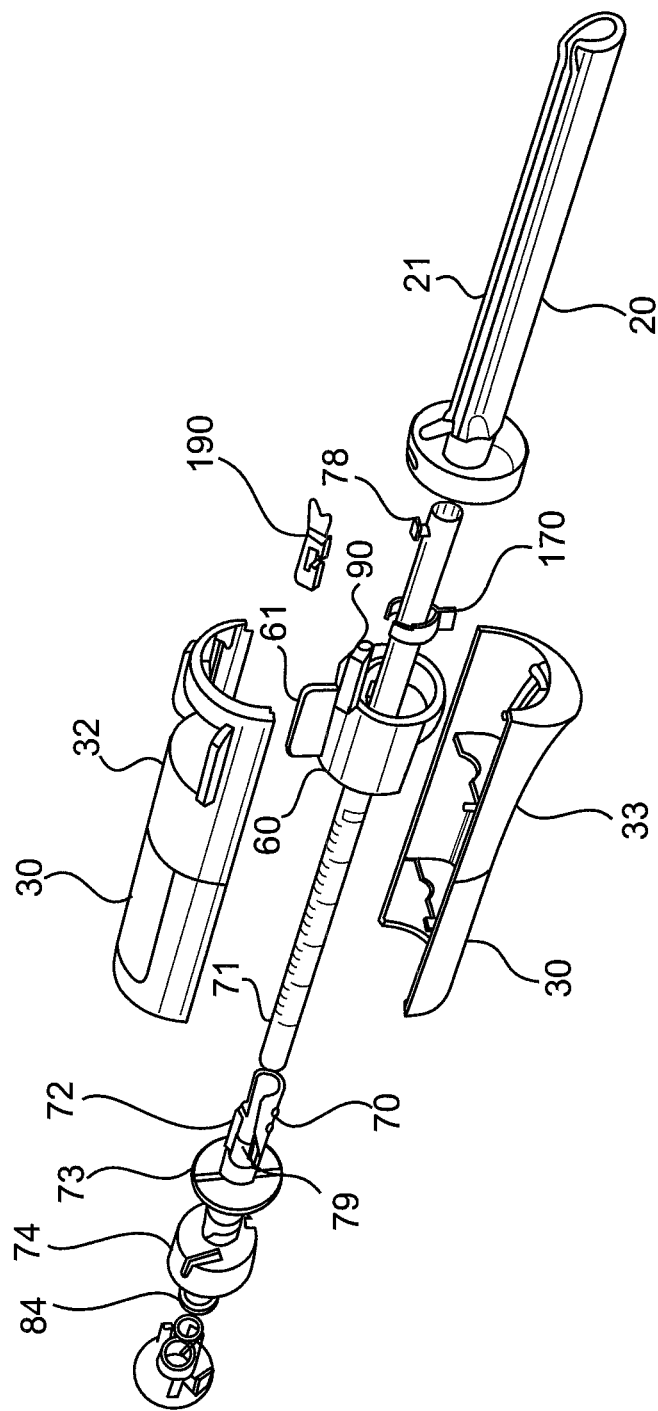
FIG. 10 is an exploded view of the embodiment depicted in FIG. 9.

FIG. 10 is an exploded view of the embodiment of the device shown in FIG. 9. FIG. 10 shows the cannula 20 which joins to the distal end of top half 32 and bottom half 33 of the housing 30. Interior to the housing 30 is the revolver 60, having a selector switch 61 for choosing the "BLADE," "SCOPE," or "SCRAPER" position of the slide lock 70, which is positioned inside the revolver 60. The blade 80 and scraper 90 tools are parked in notches 72,73 in the slide lock 70 and are retained there when not deployed by a rotary clip 170. The tube assembly 71 passes through the slide lock 70 within the housing 30. The distal end of the tube assembly 71 extends and is deployable into the cannula 20. The tube assembly 71 comprises near its distal end a tube locator 78 that the blade 80 or scraper 90 tool is engaged with for deployment into the cannula 20. The tube assembly 71 further comprises, at its proximate end, a tube stop 84 that prevents the proximate end of the tube assembly 71 from passing through the stabilizer ring 74 mounted in the rear of the housing 30. The tube assembly 71 has a longitudinal central lumen that accommodates the insertion of an endoscope through the tube assembly 71 and into the clear cannula 20 in order to visualize the tissue surrounding said cannula 20 and to observe the surgical procedure performed with the compact endoscopic surgical device. In some embodiments, the tube stop 84 is gripped by the practitioner or engaged to a grippable attachment 300 (FIG. 9) to allow the tube assembly to be operated manually for advancement or withdrawal of the tube assembly 71. In other embodiments, the tube stop 84 is engaged to an apparatus or machine for automatic or remote control of advancement or withdrawal of the tube assembly 71.

FIGS. 11A-E show details of the clear cannula element of the device. FIG. 11A shows the cannula 20 from the top, showing the slot 21 extending longitudinally from the proximity of the proximal end 22 to the proximity of the distal end 23. Also visible are the depressions, slots, or holes 26 that engage with tabs or pins on the front of the housing. In some embodiments, the sides of the slot 21 comprise texture or tick marks 27 that are at a measured distance from one another down the length of the slot 21. The tick marks 27 minimally engage with the carrier of the blade and/or scraper as it advances, or retreats, along the length of the slot 21 to allow the practitioner to feel, or otherwise determine, how far the carrier has advanced along the slot. In some embodiments, the distal end 23 of the cannula 20 is blunted and serves as an obturator.

FIG. 11B shows a side view of the cannula 20, showing the proximate 22 and distal 23 ends, as well as the depressions, slots, or holes 26 that engage with tabs or pins on the front of the housing. In some embodiments, the distal end 23 of the cannula is angled upwards, as an obturator.

FIG. 11C depicts an angled view of the clear cannula 20 of the device. In some embodiments, the depressions, slots, or holes 26 that engage with tabs or pins on the front of the housing are located on the top and bottom of the proximate end 22 of the cannula. In some embodiments, rather than individual or multiple depressions, slots, or holes 26 on the top, bottom or sides of the cannula 20, the depression 26 may be an impression or groove that runs all the way around the outside of the proximate end 22 of the cannula 20 and engages with an annular ring that runs around the inside of the distal end of the housing.

FIG. 11D shows an end view of the cannula at the proximate end 22. The view shows the slot, which is contiguous with the central lumen 28 of the cannula. FIG. 11E is a cross-sectional view of the cannula 20 at bisecting line A-A in FIG. 11A, looking towards the proximate end of the cannula 20. The longitudinal slot 21 in the top surface of the cannula 20 can be seen to be contiguous with the central lumen of the cannula tube 20.

FIGS. 12A-F show various views of the top half 32 of the housing 30. FIG. 12A shows the outside of one embodiment of the top half 32 of the housing 30 at an angle, while FIG. 12B shows the inside of one embodiment of the top half 32 of the housing 30 at an angle. FIG. 12C shows the inside of one embodiment of the top half 32 of the housing 30, showing one embodiment of a tab or pin 37 that engages with a depression, slot, or hole located on the proximate end of the cannula shown in FIGS. 11A-E. In some embodiments, rather than individual or multiple tabs or pins at the distal end of the housing, the tab 37 may be an annular ring that runs around the inside of the distal end of the housing 30 and engages an impression or groove that runs all the way around the outside of the proximate end of the cannula. FIG. 12D shows the upper half 32 of the housing 30 from a side view, while FIG. 12E shows a view of the top half 32 of the housing 30 from the distal end and FIG. 12F shows a view of the top half 32 of the housing 30 from the proximate end.

Figure 13D:
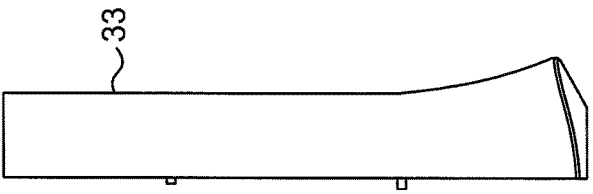
FIGS. 13A-F show perspective and cross-sectional views of the bottom shell of the housing of the embodiment depicted in FIG. 9.
Figure 13C:
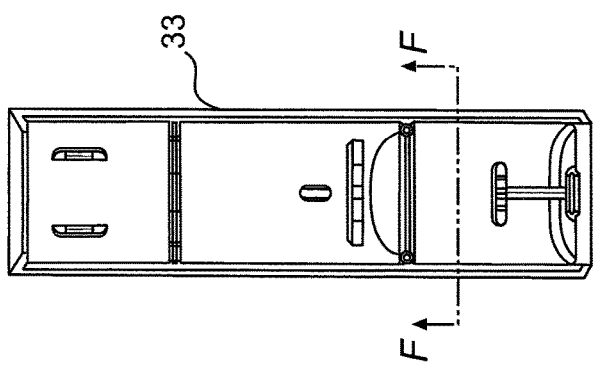
Figure 13F:
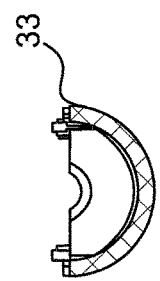
Figure 13B:
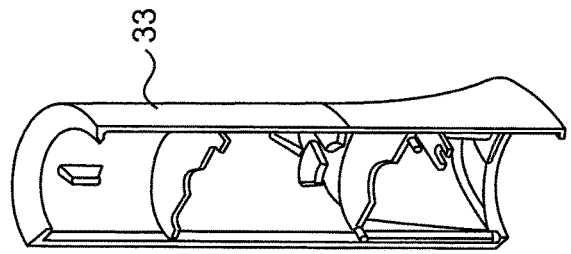
Figure 13E:
Figure 13A:
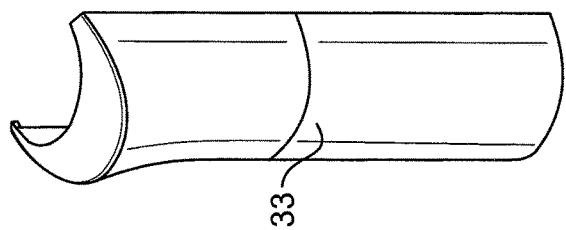

FIGS. 13A-F show various views of the lower half 33 of the housing 30. FIG. 13A shows the outside of one embodiment of the lower half 33 of the housing 30 at an angle, while FIG. 13B shows the inside of one embodiment of the lower half 33 of the housing 30 at an angle. FIG. 13C shows the inside of one embodiment of the lower half 33 of the housing 30. FIG. 13D shows the lower half 33 of the housing 30 from a side view, while FIG. 13E shows a view of the lower half 33 of the housing 30 from the distal end and FIG. 13F shows a cross-sectional view looking towards the distal end of the lower half 33 of the housing 30 from the line A-A bisecting FIG. 13C.

Figure 14C:
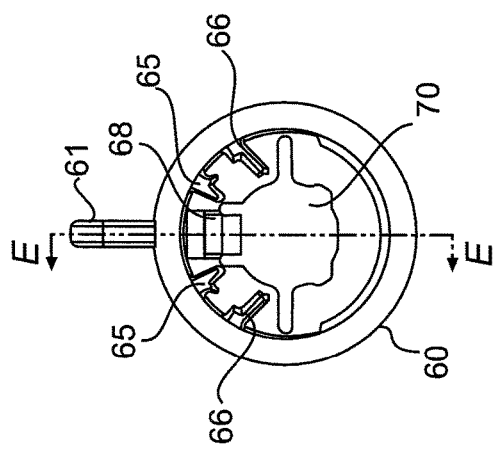
FIGS. 14A-E show perspective and cross-sectional views of the revolver element of the embodiment depicted in FIG. 9.
Figure 14B:
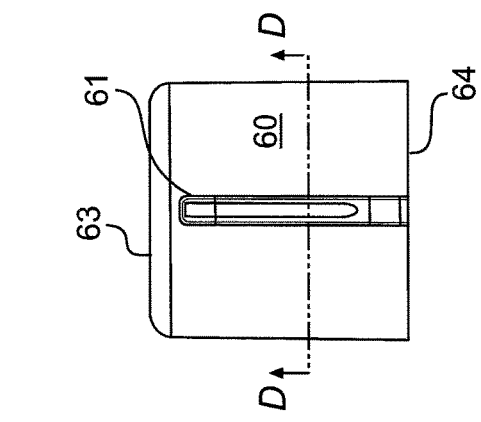
Figure 14A:
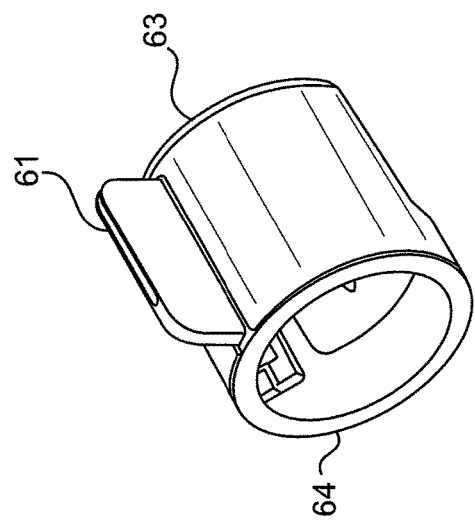

FIGS. 14A-E show detailed views of an embodiment of the revolver 60 element of the device. FIG. 14A is an exterior perspective view of the revolver 60, showing a selector switch 61 that protrudes through the opening 38 (FIG. 4) in the housing, as well as the proximate 63 and distal 64 ends of the revolver 60 element. The selector switch 61 is rotated from side to side by the user to select the appropriate instrument for a particular step in an endoscopic surgical procedure. FIG. 14B is a top view of the rotator 60 with the selector switch 61.

FIG. 14C is a view of the distal 64 end of the revolver 60. In some embodiments of the device, the revolver 60 comprises upper tabs 65 and lower tabs 66 that are used to select the scraper 90 or blade assembly 190 of the device. For example, when the selector switch 61 is rotated by the user to the position marked "SCRAPER" (see FIG. 3, for example), the tabs 65 and 66 engage the scraper 90 and move it to the centerline (here, line A-A in FIG. 14C) of the device. There, the scraper 90 is engaged by a tab on the tube (71 in FIG. 4, for example) of the device, so that it can be deployed into the cannula 20 (FIG. 4) and protrude through the longitudinal slot 21 (FIG. 4) therein. When the selector switch 61 is rotated by the user to the position marked "BLADE" (see FIG. 2, for example), the tabs 65 and 66 engage the blade assembly 190 and move it to the centerline (here, line A-A in FIG. 14C) of the device. There, the blade assembly 190 is engaged by a tab on the tube (71 in FIG. 4, for example) of the device, so that it can be deployed into the cannula 20 (FIG. 4) and protrude through the longitudinal slot 21 (FIG. 4) therein. However, when the selector switch 61 is rotated by the user to the position marked "SCOPE" (see FIG. 2, for example), the tabs 65 and 66 retain the scraper 90 and blade assembly 190 in their parked positions out of the centerline so that an endoscope, or other device, can be advanced through the tube 71 (FIG. 4) into the cannula without either the scraper tool or blade assembly being advanced.

Figure 14E:
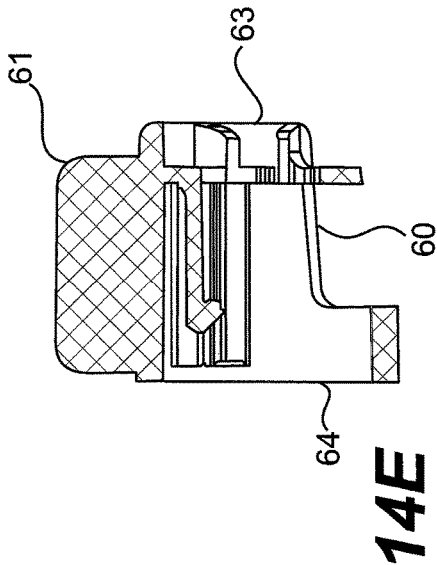
Figure 14D:
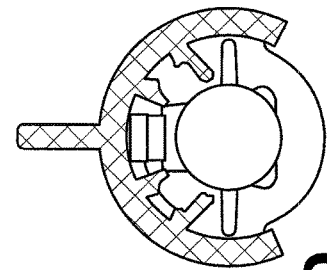

FIG. 14D is a cross-sectional view of revolver 60 at line B-B in FIG. 14B and looking in the direction of the proximate end 63 of the revolver 60. FIG. 14E is also a cross-sectional view of the revolver 60, this time along centerline A-A of FIG. 14C. As can be seen in this view, in some embodiments of the device, the revolver 60 comprises a hooked tab 68 that engages the front of the tab 79 that separates the notches (72, 73 in FIG. 10) in the slide lock 70 (see FIG. 15) that hold the scraper 90 and blade assembly 190. When the selector switch 61 is in the "SCOPE" position, for example, the hooked tab 68 helps ensure that neither the scraper tool nor blade assembly can be deployed into the cannula.

Figure 15A:
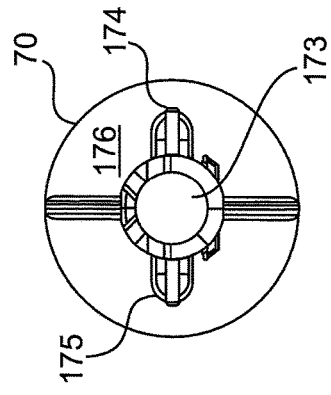
FIGS. 15A-E show perspective and cross-sectional views of the slide lock element of the embodiment depicted in FIG. 9.

Turning to FIGS. 15A-E, shown is an embodiment of a slide lock 70 of the device. FIG. 15A shows the slide lock 70 from an angled perspective. The slide lock 70 comprises two notches 72,73 that hold the scraper 90 and blade assembly 190 in place when they are parked, as well as rotate them into the ready position when they are selected for use by rotation of the revolver 60 (FIGS. 14A-E, for example). The two notches 72,73 are separated from one another by the tab 79. The front of the tab 79 engages with the hooked tab 68 (FIG. 14E, for example) of the revolver 60 when the selector switch 61 is not lined up with the "SCRAPER" or "BLADE" options, thus preventing the scraper 90 or blade assembly 190 from being deployed into the cannula when not in use. In some embodiments, the slide lock 70 comprises retaining tabs 171,172 that hold a rotary clip 170 (FIGS. 16A-E, for example) in place, preventing the rotary clip from sliding forward or backward on the slide lock 70. The rotary clip 170 does not rotate with the revolver 60 and slide lock 70, serving to prevent the scraper 90 or blade assembly 190 from sliding forward out of their notches 72,73 when they are not selected. Some embodiments of the slide lock 70 further comprise a pair of wings 174,175 that engage with the revolver 60 (FIGS. 14A-E, for example) for turning the slide lock 70 when a particular tool, such as "SCRAPER," "BLADE" or "SCOPE" is selected. Some embodiments of the slide lock 70 further comprise a disc 176 at the proximate end. The outer rim of the disc 176 contacts the inside surface of the housing 30 (FIG. 10) to allow the slide lock 70 to rotate, but prevents or constrains side-to-side or up-down movement of the slide lock in the device.

Figure 15B:
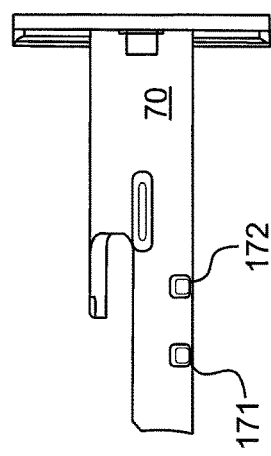
Figure 15C:
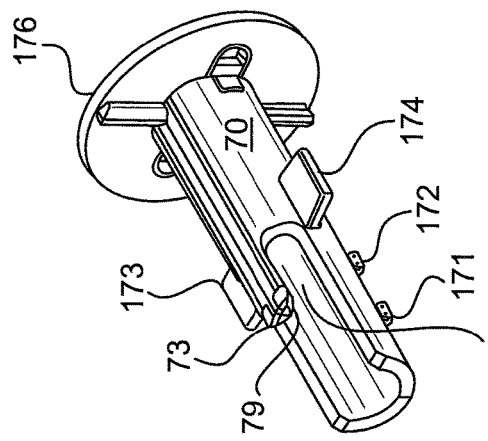
Figure 15D:
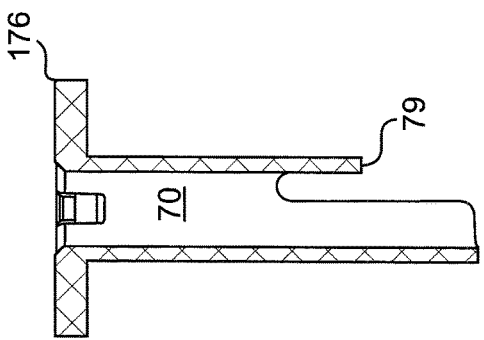
Figure 15E:
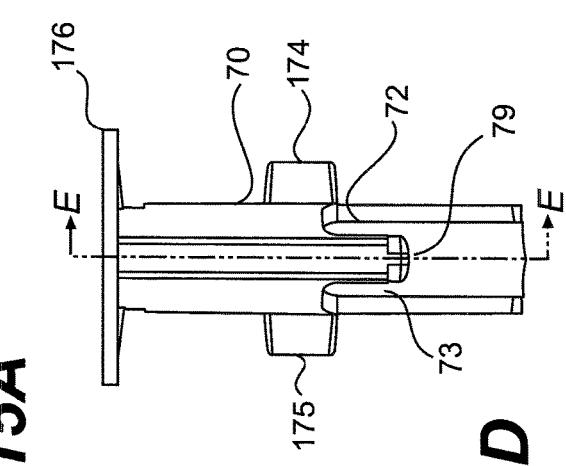

Still referring to FIG. 13, FIG. 15B is a side view of the slide lock 70. In some embodiments, the retaining tabs 171,172 are matched by identical or similar retaining tabs on the other side of the slide lock 70. FIG. 15C shows an end view of slide lock 70, looking from the distal end towards the disc 176 at the proximate end. The center lumen 173 of the slide lock 70 allows the passage of the tube assembly 71 through the slide lock 70 and into the cannula 20 (FIG. 10). FIG. 15D is a perspective view of the slide lock 70 from the top, while FIG. 15E is a longitudinal cross-section view at line A-A through FIG. 15D.

Turning now to FIGS. 16A-E, perspective views of an embodiment of a rotary clip 170 of the device are presented. FIG. 16A shows the rotary clip 170 from an angle. In some embodiments, the rotary clip 170 comprises a tab 177 that engages with the inside of the housing 30 (FIG. 10) to prevent the rotary clip 170 from rotating or sliding. The top of the rotary clip 170 is open, so that when the scraper tool or blade assembly is rotated into the deployment position, it can be deployed through the rotary clip 170 and into the cannula 20 (FIG. 10). FIG. 16B is a perspective view of the rotary clip 170 as viewed from the distal side towards the proximate side. FIG. 16C is a side perspective view of the rotary clip 170. In some embodiments, a portion of the distal side of the rotary clip 170 may be notched 179. FIG. 16D is a perspective view of the rotary clip 170 looking down upon the top. The rotary clip may be manufactured from any suitable material, such as plastic, stainless steel, aluminum, or metal alloys. In some embodiments, the rotary clip 170 may be formed, cut, stamped, cast or milled as a flat piece, as shown in FIG. 16E, from a malleable metal such as SS 303 and then formed into the final shape of being an open-topped ring with a tab at the bottom as shown in FIG. 16A. In other embodiments, the rotary clip 170 may be formed, cut, molded, 3D-printed, cast or milled from a suitable material as an open-topped ring with a tab at the bottom as shown in FIG. 16A.

FIGS. 17A-D show an embodiment of a tube assembly 71 of the device. In some embodiments, the tube assembly is composed of stainless steel, preferably AISI 304 stainless steel. However, the tube assembly can be made from any suitable material including, but not limited to, aluminum, titanium, nitinol or other metal alloys, or plastic. In some embodiments where the tube assembly 71 is made of plastic, the plastic may be clear, allowing visualization with an endoscope of tissues surrounding the cannula 20 through the body of the tube assembly 71.

FIG. 17A is a top view of the tube assembly 71. The body of the tube assembly 71 slides through the center lumen 173 of the slide lock 70. The tube assembly 71 comprises near its distal end a tool selector 78. The tool selector 78 is directly on top of the tube assembly 71. With reference to FIGS. 9 and 10, when the selector switch 61 of the revolver 60 is positioned at the "SCOPE" setting, no tools are engaged with the tool selector 78 and the tube assembly 71 can be advanced into the cannula 20 without the blade assembly 190 or scraper 90. When the selector switch 61 of the revolver 60 is mover to the "BLADE" setting, the revolver 60 rotates the slide lock 70 such that the notch 72 holding the blade assembly 190 is moved to the top of the tube assembly 71 and the notch in the bottom surface of the blade assembly 190 is positively engaged with the tool selector 78. Advancement of the tube assembly 71 would cause the advancement of the blade assembly 190 into and down the length of the cannula 20, protruding through the slot 21. When the selector switch 61 of the revolver 60 is mover to the "SCRAPER" setting, the revolver 60 rotates the slide lock 70 such that the notch 73 holding the scraper 90 is moved to the top of the tube assembly 71 and the notch in the bottom surface of the scraper 90 is positively engaged with the tool selector 78. Advancement of the tube assembly 71 would cause the advancement of the scraper 90 into and down the length of the cannula 20, protruding through the slot 21. In some embodiments, the tool selector 78 is welded, preferably laser welded, onto the top of the tube element of the tube assembly 71. In a preferred embodiment, the tool selector 78 is welded all around at its base to the tube element. In particular embodiments, the strength of the weld should be able to withstand the application of 5 in-lbs torque to the unit, more particularly 10 in-lbs torque. The tube assembly 71 further comprises a tube stop 84 at the proximate end of the tube element. The tube stop 84 retains the tube assembly 71 in the housing 30 of the device, preventing the tube assembly from passing completely through the stabilizer disc 74 (FIG. 10) at the proximate end of the housing 30. In some embodiments, the tube stop 84 is welded flush with the proximate end of the tube element of the tube assembly. In particular embodiments, the weld should be strong enough to withstand at least 10 lbs normal force to the face, more particularly 20 lbs normal to the face. In some embodiments, the proximate portion of the tube assembly.

The tube assembly 71 can optionally be marked on the top or side surface with gradations 86,87 as exemplified in FIG. 17A to show the distance that the tube assembly 71 has been advanced into the cannula 20. As a non-limiting example, major gradations 86 can be made to show each centimeter in distance that the tube assembly 71 has been advanced into the cannula 20, with minor gradations 87 between them to show, for example, each 1, 2, 2.5 or 5 millimeters. While the gradations can be applied to the tube assembly 71 by any means known in the art, it is preferable to lasermark the gradations on the tube assembly 71 for accuracy and permanence. In some embodiments, the distance between the major or minor gradations 86,87 corresponds to the distance between the tick marks 27 (FIG. 11A) in the sides of the slot 21 in the cannula 20.

FIG. 17 B shows a cross-section of the tube assembly 71 at the line bisecting FIG. 17A at A-A and looking in the direction of the tube stop 84 at the proximate end. The tube assembly 71 has a central lumen 85 that accommodates the insertion and free passage of an endoscope or other viewing device or tool, for example. FIG. 17C is a side view of the tube assembly 71 and FIG. 17 D is a perspective view of the tube assembly 71 from an angle.

FIGS. 18A-C show an embodiment of the blade assembly 190, comprising a pusher base 191 and a cutting blade 200. FIG. 18A is a side perspective view of the blade assembly 190. The pusher base 191 comprises a notch 192 that positively engages with the tool selector 78 of the tube assembly (FIGS. 17A, C and D). When the selector switch 61 of the revolver 60 (FIG. 10) is rotated to the "BLADE" position, the blade assembly 190 is rotated upward by the slide lock 70 so that the notch 192 in the base of the blade assembly 190 slides onto and engages the tool selector 78. The tool selector 78 then firmly holds the blade assembly 190 on the surface of the tube assembly 71. Advancing the tube assembly 71 also advances the blade assembly 190 into the cannula 20 (FIG. 10). The blade assembly 190 protrudes through the longitudinal slot 21 in the cannula 20 and advancement of the blade assembly 190 with the tube assembly 71 moves the blade 200 into contact with the target tissue. Further advancement of the blade assembly allows the blade 200 to separate the target tissue. In preferable embodiments, the bottom surface 210 of the blade 200 is at least slightly above the bottom surface 193 of the pusher base 191 so that the blade 200 does not directly contact the body of the tube assembly 71, which may affect rotation of the blade assembly 190 into place for deployment. In particular embodiments, the end of the pusher base opposite the blade 200 is angled so that it does not catch tissues as it is being withdrawn through the slot 21 of the cannula 20. FIG. 18B is an end view of the blade assembly 190. The width of the pusher base 191 is such that it securely contacts the side walls of the slot 21 in the cannula 20 (FIG. 10) but is still able to be advanced or withdrawn through the slot without an amount of friction that would impede its progress. The sides of the blade 200 do not contact the walls of the slot 21. In particular embodiments, the bottom surface 194 of the pusher base is curved to match the curvature of the tube assembly, thus inhibiting or preventing side to side motion, or wobble, of the blade assembly 190 during deployment. FIG. 18C is an angled perspective view of the blade assembly 190. The view is clear so that the attachment of the blade 200 to the pusher base 191 can be seen. In particular embodiments, the blade 200 comprises a tab 215 that embeds into the pusher base 191. In particular embodiments there is a hole 220 in the tab 215 that allows the material of the pusher base 191 to flow through it when the pusher base 191 is cast, thereby securing the tab 215 into the pusher base 191. In some embodiments, the tab 215 is secured into the pusher base 191 using a pin or screw. In such an embodiment, the blade 200 may be replaceable in the blade assembly, allowing the use of blades with different profiles particularly suited for a specific surgical procedure. For example, it may be desirable to use a hook blade in some situations, where the cutting surface faces back towards the housing 30 of the device, allowing the practitioner to move the blade past the target tissue and separate the target tissue by pulling the blade backwards, rather than separating the target tissue upon advancing the blade. The pusher base 191 of the blade assembly 190 can be formed of any medically acceptable material, such as a plastic, as it does come in contact with body tissues. In a particular embodiment, the pusher base 191 is formed of polycarbonate. In some embodiments, the blade assembly 190 may be replaced in the device with any other suitable blade tool that engages with the tool selector, such as, but not limited to, the blade 80 shown in FIG. 4 or a hooked endoscopic blade tool.

FIGS. 19A-E show a particular embodiment of the blade 200. FIG. 19A shows a side view of the blade 200 embodiment. In a particular embodiment, the blade 200 as shown in FIG. 19A comprises an upper cutting surface 1 on the leading end of the blade, which is at an angle 2 with respect to the horizontal orientation of the blade 200, as defined by the bottom surface 210 of the blade 200. The angle 2 is such that the top of cutting surface 1 is forward of the bottom of the cutting surface. In one embodiment the angle 2 is between about 30 and about 45 degrees. In a particular embodiment, the angle 2 is between about 30 and about 40 degrees. In another particular embodiment, the angle 2 is between about 33 and about 39 degrees. In a more particular embodiment, the angle 2 is about 36 degrees.

In some embodiments, the upper end 3 of the cutting surface 1 is radiused. The radiused upper end 3 of the cutting surface 1 is about 90 degrees of a circle and has a radius measurement between about 0.50 mm and 1.50 mm. In a particular embodiment, the radius is about 0.94 mm.

In a particular embodiment, the blade 200 as shown in FIG. 19A comprises a lower cutting surface 4 on the leading end of the blade, which is at an angle 5 with respect to the horizontal orientation of the blade 200, as defined by the bottom surface 210 of the blade 200. The angle 5 is such that the bottom of the lower cutting surface 4 is forward of the top of the lower cutting surface. In one embodiment the angle 5 is between about 45 and about 65 degrees. In a particular embodiment, the angle 5 is between about 50 and about 60 degrees. In a more particular embodiment, the angle 5 is about 54 degrees. In some embodiments, the bottom of the lower cutting surface 4 is not radiused, as the bottom of the lower cutting surface 4 remains within the slot 21 of the cannula 20 (FIG. 10) during deployment.

In a particular embodiment, the blade 200 as shown in FIG. 19A comprises upper cutting surface 1 and lower cutting surface 4 on the leading end of the blade 200, which are at an angle 6 to one another and meet at a central crotch 7. In one embodiment the angle 6 is between about 80 and about 100 degrees. In a further embodiment, the angle 6 is between about 85 and about 95 degrees. In a still further embodiment, the angle 6 is about 90 degrees.

Still referring to FIG. 19A, in some embodiments, the plane where the upper and lower cutting surfaces meet is angled downward 8 towards the crotch 7. In some embodiments, the angle 8, as it relates to the plane defined by the bottom surface 210 of the blade, is between about 0 and 20 degrees. In further embodiments, the angle 8, as it relates to the plane defined by the bottom surface 210 of the blade, is between about 5 and 15 degrees. In a particular embodiment, the angle 8, as it relates to the plane defined by the bottom surface 210 of the blade, is about 9 degrees. In particular embodiments, the crotch 7 is ground to have a maximum radius of between about 0.18 mm and about 0.58 mm, more particularly between about 0.28 mm and about 0.48 mm. In a still more particular embodiment, the crotch 7 is ground to have a maximum radius of about 0.381 mm.

In some embodiments, in order to prevent the blade 200 from catching on tissues when the blade 200 is drawn backwards through the cannula 20, the top surface 211 of the blade 200 is angled downward and may comprise a further stepped angle 212, before fully descending 213 to meet the top edge 214 of the tab 215 that secures the blade 200 into the pusher base 191. In a particular embodiment, the vertical height of the radius 3 at the top end of the upper cutting surface 1 above the top edge 214 of the tab 215 is between about 0.75 mm and about 1.75 mm, more particularly between about 1.0 mm and about 1.50 mm. In a more particular embodiment, the vertical height 229 of the radius 3 at the top end of the upper cutting surface 1 above the top edge 214 of the tab 215 is about 1.26 mm.

Additionally, in some embodiments, the trailing end 216 of the bottom surface 210 of the blade 200 may be angled up to the bottom edge 217 of the tab 215. In a particular embodiment, the vertical height between the bottom surface 210 of the blade 200 and the bottom edge 217 of the tab 215 is between about 0.1 mm and about 1.0 mm, more particularly between about 0.3 mm and about 0.7 mm. In a more particular embodiment, the vertical height between the bottom surface 210 of the blade 200 and the bottom edge 217 of the tab 215 is about 0.5 mm.

Still referring to FIG. 19A, in some embodiments, the tab 215 is between about 1.5 mm and about 2.0 mm high between the top edge 214 and bottom edge 217 of the tab 215, more particularly between about 1.65 mm and about 1.85 mm. In a still more particular embodiment, the tab 215 is about 1.75 mm high between the top edge 214 and bottom edge 217 of the tab 215. Additionally, in some embodiments, the tab 215 is between about 2.0 mm and about 3.0 mm long between where it meets the top surface 211 of the blade 200 (at 213) and the trailing edge 218 of the tab 215, more particularly between about 2.25 mm and about 2.75 mm. In a still more particular embodiment, the tab 215 is about 2.5 mm long between where it meets the top surface 211 of the blade 200 (at 213) and the trailing edge 218 of the tab 215. The hole 220 in the tab 215 that serves to secure the blade 200 into the pusher base 191 (FIG. 18C) is generally centered horizontally and vertically in the tab 215 in order to provide maximum adhesion of the tab 215 to, and stability within, the pusher base 191. The diameter of the hole 220 is between about 0.5 mm and about 1.5 mm, more particularly between about 0.75 mm and about 1.25 mm. In a more particular embodiment, the diameter of the hole 220 is about 1.0 mm.

In some embodiments, the crotch 7 of the blade 200 is between about 3.0 mm and about 7.5 mm forward of the trailing edge 218 of the tab 215, more particularly between about 4.0 mm and about 6.5 mm. In a still more particular embodiment, the crotch 7 of the blade 200 is about 5.25 mm forward of the trailing edge 218 of the tab 215.

In particular embodiments, the blade 200 is made from stainless steel. In a further embodiment, the stainless steel is martensitic stainless steel. An exemplary martensitic stainless steel is Bohler-Uddeholm AEB-L martensitic stainless steel. In a still further embodiment, the martensitic stainless steel is heat-treated. In another further embodiment, the stainless steel is 440 A stainless steel. In a particular embodiment, the blade is made from Hitachi GIN-5 SST-MODI-FIED 440-A stainless steel. The blade is optionally flash electropolished or passivated per ASTM A967, or by any other method that delivers a similar finish. The cutting edges are machine finished and must be sharp. In a particular embodiment, the steel of the blade is heat-treated to Rockwell C hardness of about 50-72. In a more particular embodiment, the steel of the blade is heat-treated to R30N 75.7-77.5 (Rockwell C hardness of 58-60).

Referring now to FIG. 19B, the lower cutting surface 4 is a single beveled cutting surface and the angle 9 is between about 30 degrees and about 50 degrees. In some embodiments, the angle 9 is between about 35 degrees and about 45 degrees. In a particular embodiment, the angle 9 is about 40 degrees. While not shown in the figure, the upper cutting surface 1 is a similarly a single beveled cutting surface and the angle is between about 30 degrees and about 50 degrees. In some embodiments, the angle is between about 35 degrees and about 45 degrees. In a particular embodiment, the angle is about 40 degrees.

Also referring to FIG. 19B, in some embodiments, the depth of the grind 225 of lower cutting surface 4, as well as for upper cutting surface 1, is between about 0.6 mm and about 1.1 mm. In other embodiment, the depth of the grind 225 is between about 0.7 mm and about 1.0 mm. In a further embodiment, the depth of the grind 225 is about 0.86 mm.

Referring now to FIG. 19C, in a particular embodiment, the overall height 226 of the body of the blade 200 is between about 3.0 mm and about 4.0 mm. In another embodiment, the height 226 of the body of the blade 200 is between about 3.25 mm and about 3.75 mm. In a more particular embodiment, the height 226 of the body of the blade 200 is about 3.5 mm. Again referring to FIG. 1C, in a particular embodiment, the width 227 of the body of the blade 200 is between about 0.3 mm and about 0.9 mm. In another embodiment, the width 227 of the body of the blade 200 is between about 0.45 mm and about 0.75 mm. In a particular embodiment, the width 227 the body of the blade 200 is about 0.635+/−0.025 mm.

Referring to FIG. 19D, the total length 228 of the blade 200 from the leading point of the upper cutting surface 1 to the trailing end 218 of the tab 215 is between about 4 mm and about 10 mm. In another particular embodiment, the total length 228 of the blade 200 from the leading point of the upper cutting surface 1 to the trailing end 218 of the tab 215 is between about 5.5 mm and about 8.5 mm. In a more particular embodiment the total length 228 of the blade 200 is about 7.153 mm. FIG. 19E presents an angled perspective view of an embodiment of the blade 200.

Figure 20:
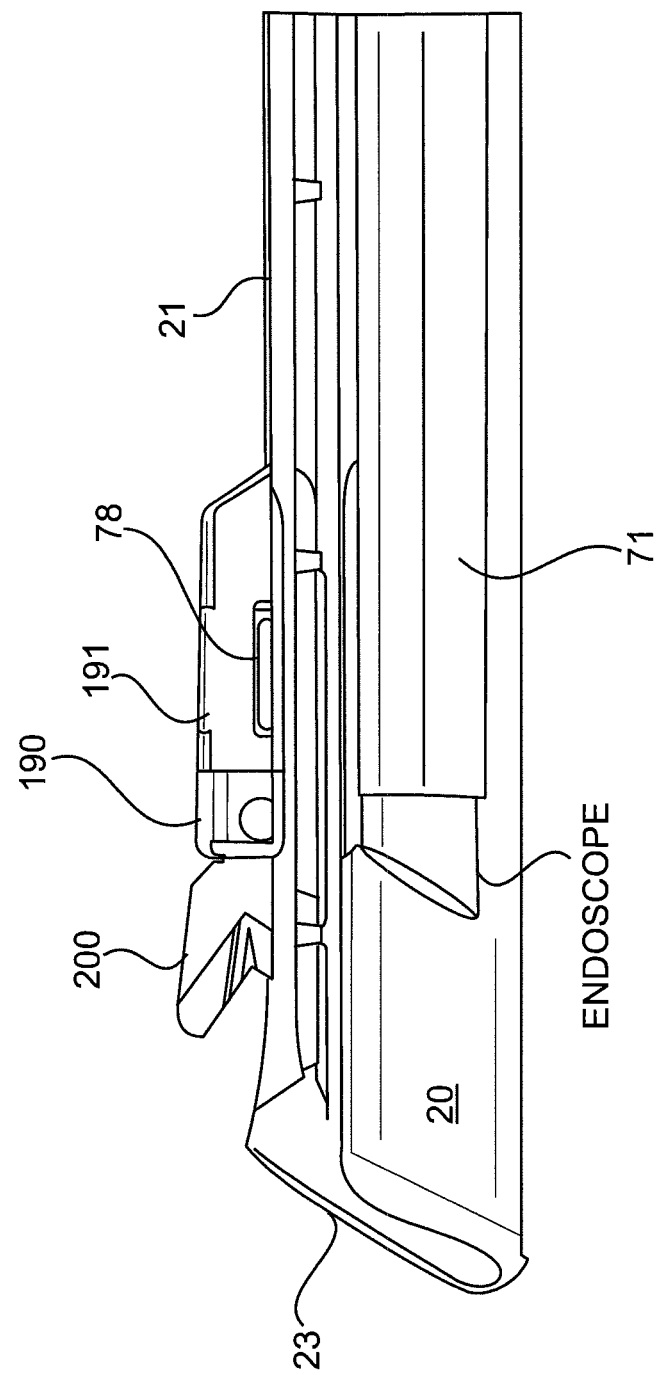
FIG. 20 shows a perspective view of the blade element of the embodiment depicted in FIG. 9, as deployed through the slot in the cannula.
Figure 21:
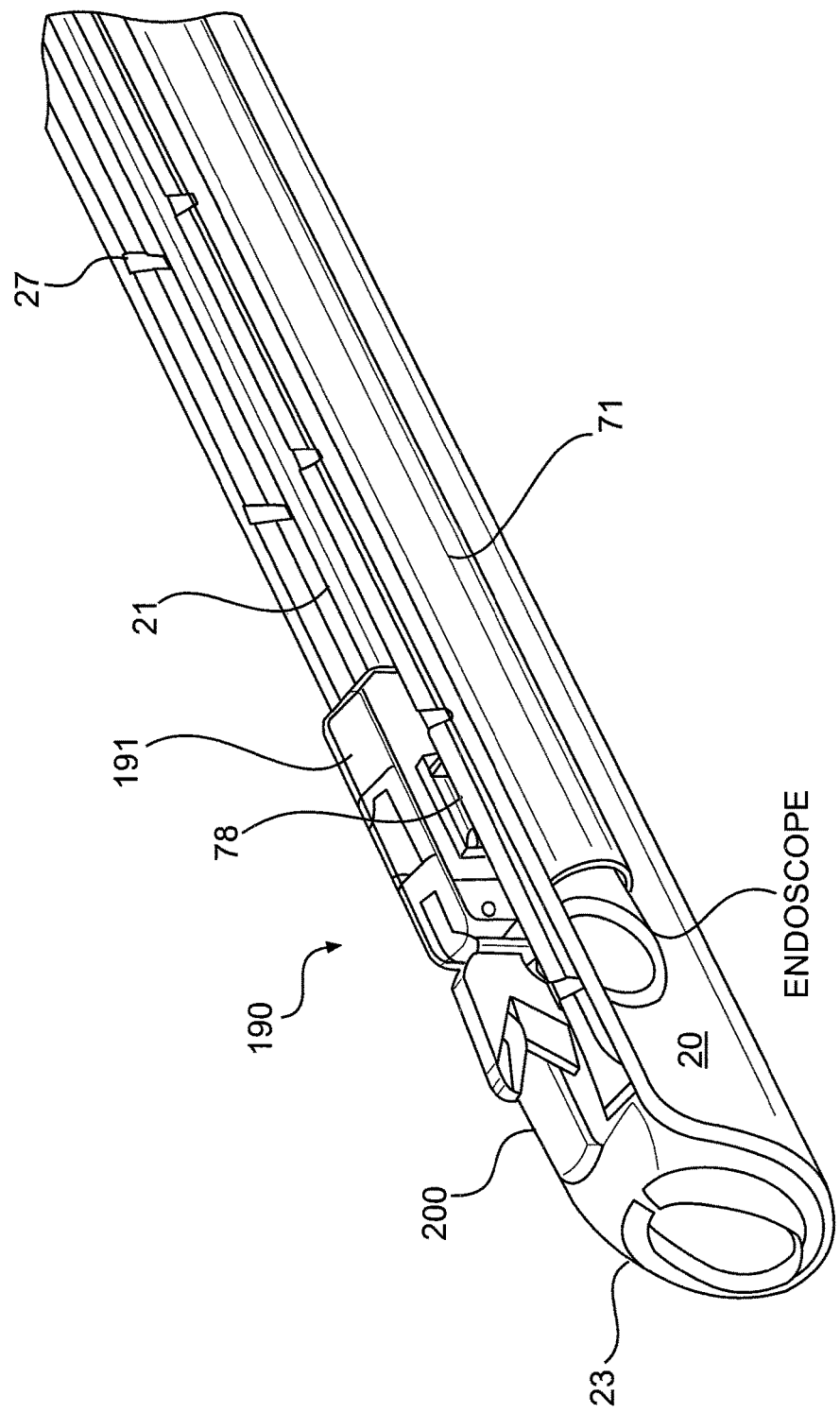
FIG. 21 shows another perspective view of the blade element of the embodiment depicted in FIG. 9, as deployed through the slot in the cannula.

FIGS. 20 and 21 show perspective views of the blade assembly 190 deployed into the cannula 20 of the device. Tube assembly 71 can be seen within the lumen of the cannula 20 with an endoscope extended through the tube assembly 71. The tool selector 78 is positively engaged with the pusher base 191 of the blade assembly 190. The pusher base 191 and blade 200 are seen partially protruding from the slot 21 in the cannula 20, but are securely held in the slot 21 by the tool selector 78 of the tube assembly 71.

Figure 22:
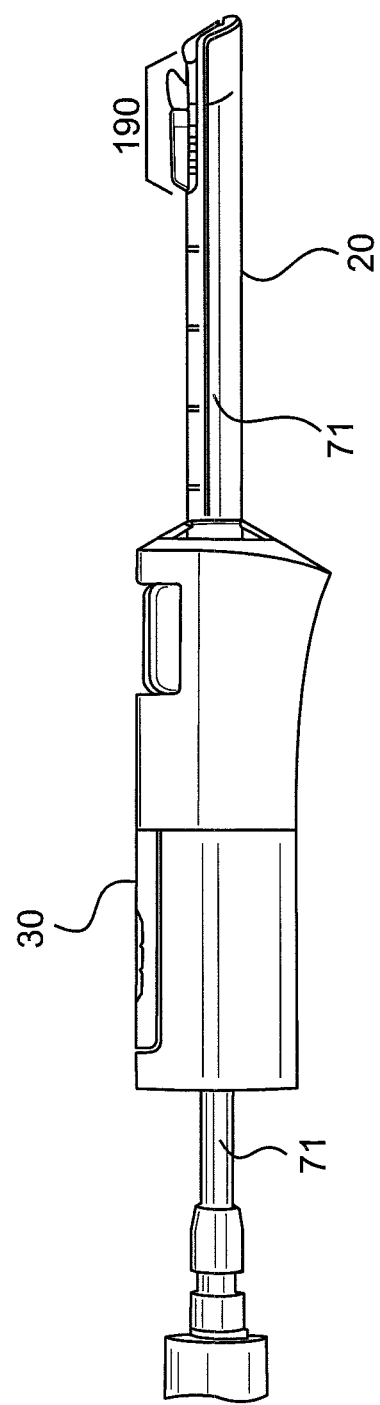
FIG. 22 shows a side perspective view of the embodiment depicted in FIG. 9 with the blade deployed through the slot in the cannula.

FIG. 22 is another perspective view showing the assembled compact endoscopic surgical device of FIG. 9 with the blade assembly 190 deployed.

Figure 23A:
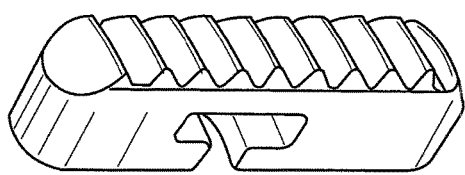
FIGS. 23A-E show perspective views of the scraper element of the embodiment depicted in FIG. 9.

FIGS. 23A-E show an embodiment of the scraper 90 of the compact endoscopic surgical device. As seen in FIG. 23A, the base 91 of the scraper 90 comprises a notch 92 that positively engages with the tool selector 78 of the tube assembly (FIGS. 17A, C and D). When the selector switch 61 of the revolver 60 (FIG. 10) is rotated to the "SCRAPER" position, the scraper 90 is rotated upward by the slide lock 70 so that the notch 92 in the base 91 of the scraper 90 slides onto and engages the tool selector 78. The tool selector 78 then firmly holds the scraper 90 on the surface of the tube assembly 71. Advancing the tube assembly 71 also advances the scraper 90 into the cannula 20 (FIG. 10). The teeth 93 of the scraper 90 protrude through the longitudinal slot 21 in the cannula 20 and advancement of the scraper 90 with the tube assembly 71 moves the teeth 93 into contact with the target tissue. Further advancement of the blade assembly allows the teeth 93 to rake across the target tissue. In particular embodiments, the distal end 94 and proximate end 95 of the base 91 are rounded and angled downwards so that they do not catch tissues as the scraper 90 is being advanced or withdrawn through the slot 21 of the cannula 20.

Figure 23B:
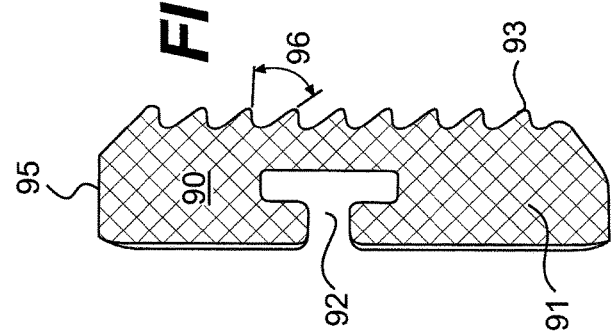

FIG. 23B is an end view of the scraper tool 90. The width of the base 91 is such that it securely contacts the side walls of the slot 21 in the cannula 20 (FIG. 10) but is still able to be advanced or withdrawn through the slot without an amount of friction that would impede its progress. In particular embodiments, the bottom surface of the base 91 is curved to match the curvature of the tube assembly, thus inhibiting or preventing side to side motion, or wobble, of the scraper 90 during deployment.

Figure 23C:
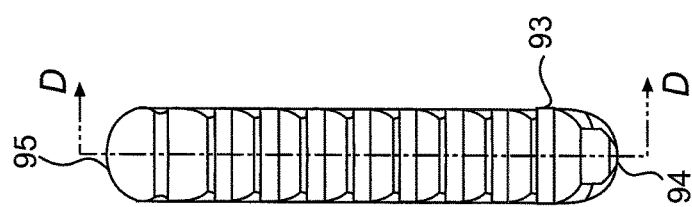
Figure 23D:
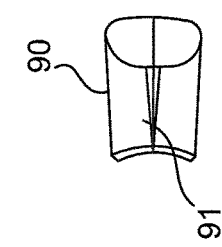
Figure 23E:
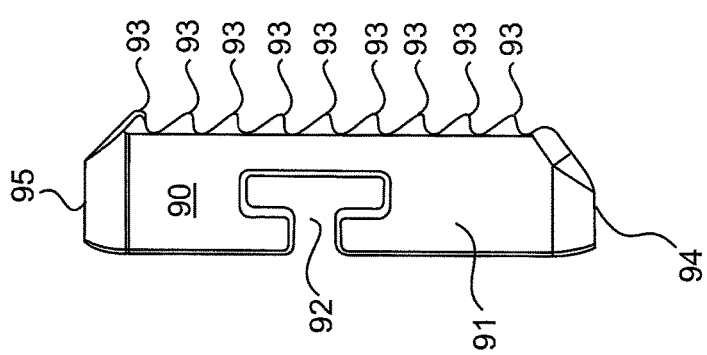

FIG. 23C is a perspective view of the top of the scraper 90 showing the linear arrangement of the teeth 90. FIG. 23D is a cross-sectional view of the scraper 90 at the line A-A through FIG. 23C. In some embodiments, the teeth are angled 96 to each other at between about 45 degrees and 75 degrees, more particularly between about 55 degrees and about 65 degrees. In a still more particular embodiment, the teeth 93 are angled 96 to each other at about 60 degrees. In some embodiments the teeth 93 are between about 1.0 mm and about 6.0 mm in height, more particularly between about 2.0 mm and about 4.0 mm. In a still more particular embodiment, the teeth 93 are about 3.23 mm in height. FIG. 23E is a perspective view of the scraper 90 from an angle. The scraper 90 can be formed of any medically acceptable material, such as a plastic, stainless steel, or nitinol, as it does come in contact with body tissues. In a particular embodiment, scraper 90 is formed of polycarbonate.

Figure 24:
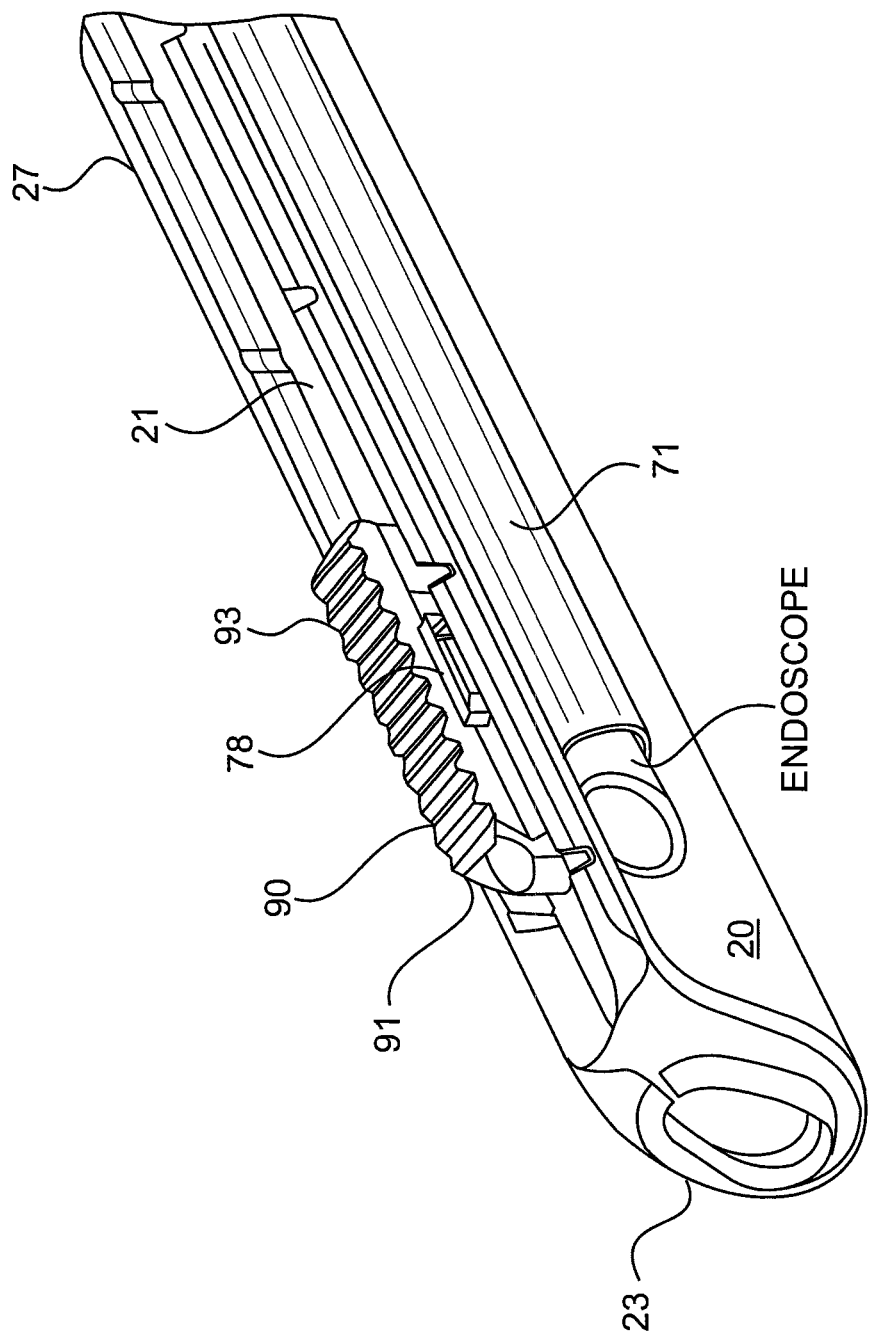
FIG. 24 shows a perspective view of the scraper element of the embodiment depicted in FIG. 9, as deployed through the slot in the cannula.

FIG. 24 shows a perspective views of the scraper 90 deployed into the cannula 20 of the device. Tube assembly 71 can be seen within the lumen of the cannula 20 with an endoscope extended through the tube assembly 71. The tool selector 78 is positively engaged with the scraper 90. The base 91 of the scraper 90 is seen partially protruding from the slot 21 in the cannula 20, but is securely held in the slot 21 by the tool selector 78 of the tube assembly 71. The teeth 93 are fully exposed to the environment outside the cannula 20 when deployed.

Figure 25:
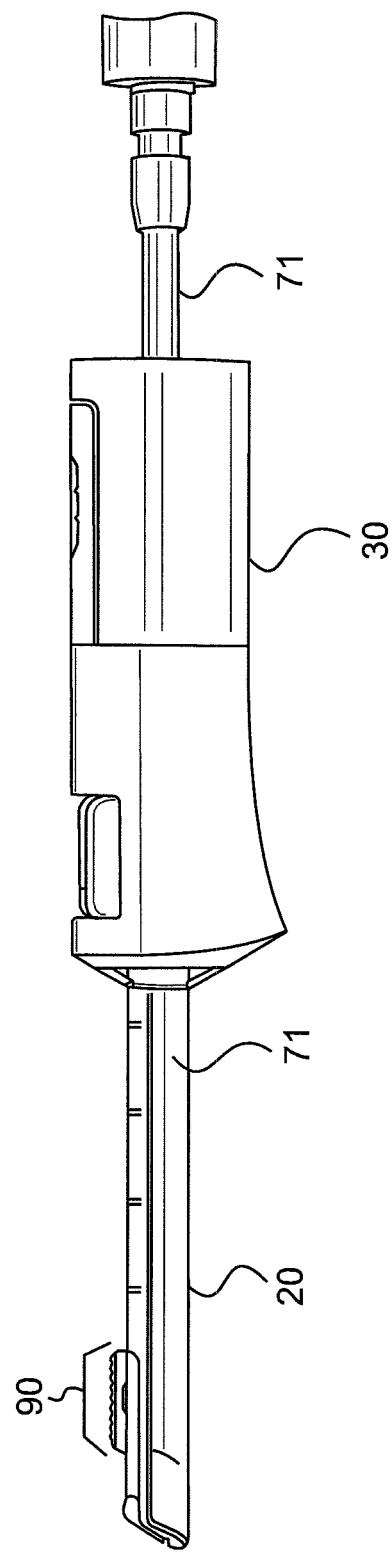
FIG. 25 shows a side perspective view of the embodiment depicted in FIG. 9 with the scraper deployed through the slot in the cannula.
Figure 26:
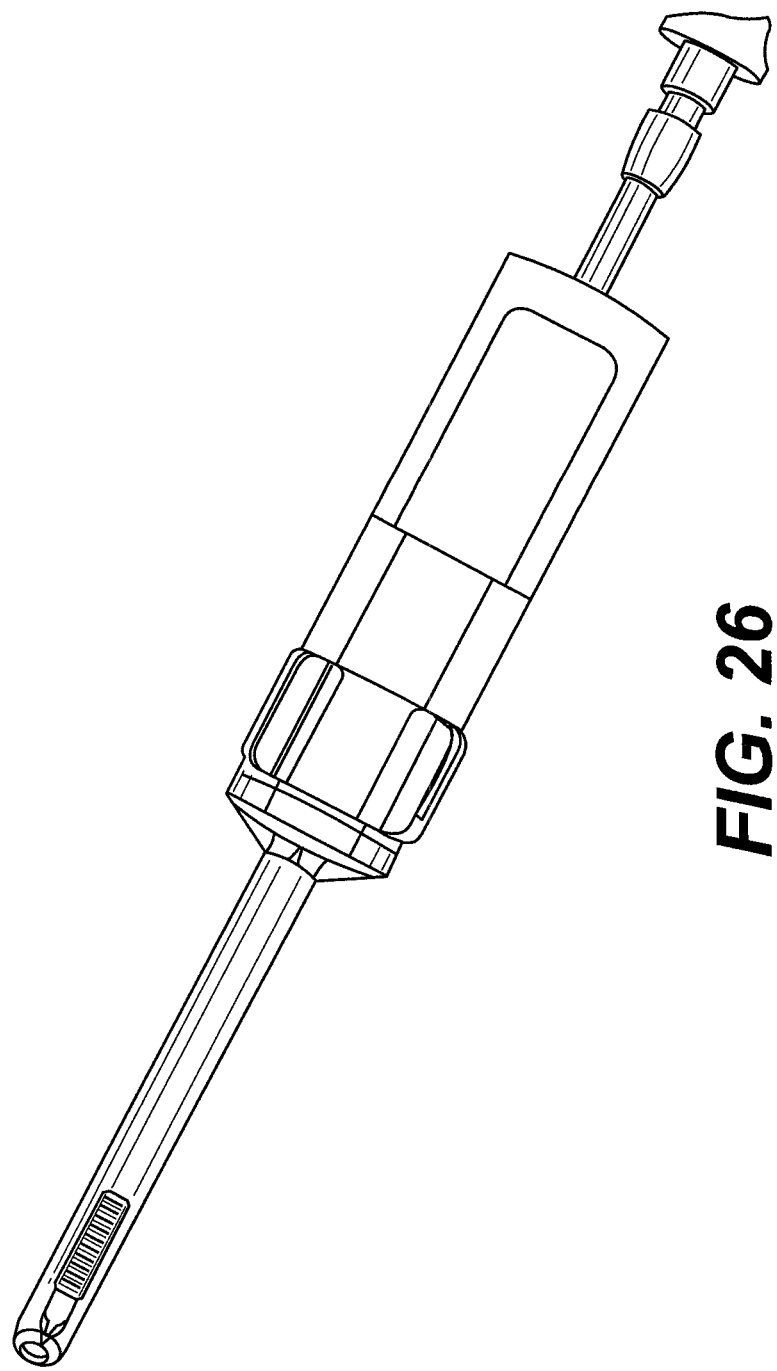
FIG. 26 shows a top perspective view of the embodiment depicted in FIG. 9 with the scraper deployed through the slot in the cannula.

FIG. 25 is a side perspective view showing the assembled compact endoscopic surgical device of FIG. 9 with the scraper 90 deployed. FIG. 26 is a top perspective view showing the assembled compact endoscopic surgical device of FIG. 9 with the scraper 90 deployed.

Kit

Another aspect of the present application relates to an instrument kit for implementing an endoscopic surgical procedure. The instrument kit contains an endoscopic surgical device comprising a slotted clear cannula, a blade and a housing, wherein the cannula is attached to the housing, and further wherein the blade is enclosed in the housing and is slidable into the cannula.

In some embodiments, the endoscopic surgical device comprises a slotted clear cannula, a scraper, a blade and a housing, wherein, the cannula is attached to the housing, in a pre-deployment configuration the scraper and the blade are enclosed in the housing, the blade and scraper are individually selectable for deployment orientation, and in deployment orientation the blade or scraper are slidable into the cannula.

In some embodiments, the instrument kit comprises components and implements useful for endoscopic procedures.

In one embodiment, the instrument kit further includes an endoscope sized for insertion into the slotted clear cannula for direct visualization of an operative site.

In another embodiment, the instrument kit further includes a scalpel.

In another embodiment, the instrument kit further includes an elevator.

In another embodiment, the instrument kit further includes a depth gauge mountable to a leading end of the endoscope.

In another embodiment, the instrument kit further includes a stop device mountable on or in the cannula to prevent excessive penetration at a surgical site by the cutting instrument.

In another embodiment, the instrument kit further includes a curved dissector.

Method for Endoscopic Surgery

Another aspect of the present application relates to a method for uniportal endoscopic surgery. Uniportal endoscopic surgery allows the practitioner to visualize a target tissue and its surrounding tissues as well as perform a surgical procedure through a single entry portal. In some instances, the entry portal may be a natural opening, while in other instances the entry portal is an incision. In the case of an incision, generally only a single small incision must be made. In particular embodiments, the incision is less than or equal to about 2 cm in length. In more particular embodiments, the incision is less than or equal to about 1.5 cm in length. In still more particular embodiments, the incision is less than or equal to about 1 cm in length. The single small incision allows the patient to recover more quickly and begin therapy and/or resume normal activity as tolerated sooner.

The uniportal endoscopic surgical procedure described herein can be used to implement a number of different surgical procedures including, but not limited to, carpal tunnel release, Guyon's tunnel (or canal) release, cubital tunnel release, plantar fascia release, lateral release for patella realignment, release of radial tunnel, release of pronatar teres, release of trigger finger, release of lacertus fibrosus, release of the extensor tendons for lateral epicondylitis, release of medial epicondylitis, release of the posterior and other compartments of the leg, forearm fascia release for fascial compartment syndrome, release of fascial compartments in the upper or lower extremities, relieving the compression of a nerve by a ligament pulley or tunnel, and releasing the travel of a ligament through a ligament pulley or tunnel.

One embodiment of the present application relates to a method for a performing a uniportal endoscopic surgical procedure a target tissue in a subject. Generally, following the establishment of an entry portal, in some embodiments a blunt instrument, such as an elevator is inserted through the portal to establish an opening in the underlying tissue between the portal and the target tissue.

In one embodiment, an endoscopic surgical device comprising a slotted clear cannula, a blade and a housing, wherein the cannula is attached to the housing, and further wherein the blade is enclosed in the housing and is slidable into the cannula, is inserted into the entry portal and extended through to the target tissue.

In some embodiments, the endoscopic surgical device comprises a slotted clear cannula, a scraper, a blade and a housing, wherein, the cannula is attached to the housing, in a pre-deployment configuration the scraper and the blade are enclosed in the housing, the blade and scraper are individually selectable for deployment orientation, and in deployment orientation the blade or scraper are slidable into the cannula.

An endoscope is inserted through the housing and into the cannula to view the target tissue and the surrounding tissues, assuring that the slot of the cannula is in proper orientation to the target tissue.

The paddle of the endoscopic surgical device is released from its locked or parked position and advanced along the slot in the housing so that the knife is advanced further through the cannula so that the blade moves in contact with the target tissue through the slot, operatively engaging the target tissue with the blade. The blade is further advanced through the cannula to divide the target tissue.

In one particular embodiment, the operative procedure is trigger finger release.

In another particular embodiment, the establishing an entry portal comprises making an incision.

In another particular embodiment, the target tissue is the A1 pulley.

The present invention is further illustrated by the following examples which should not be construed as limiting. The contents of all references, patents and published patent applications cited throughout this application, as well as the Figures and Tables, are incorporated herein by reference.

EXAMPLE 1

UNIPORTAL ENDOSCOPIC TRIGGER RELEASE

In a patient presenting with trigger finger of the middle or ring finger, a 1 cm incision is made just proximal to the A1 pulley on the distal palmar crease proximate to the affected digit.

An elevator is introduced into the incision and used to create a plane superficial to the flexor tendon sheath. The elevator is withdrawn.

The cannula portion of an endoscopic surgical device comprising a slotted clear cannula, a scraper, a blade and a housing, wherein the cannula is attached to the housing, and further wherein the scraper and blade are enclosed in the housing, are individually selectable for deployment and are slidable into the cannula is introduced into the incision and advanced through the plane created by the elevator. The slot of the cannula is oriented facing the flexor tendon sheath.

The revolver of the device is set to allow the advancement of the endoscope without the deployment of the blade or scraper. The endoscope is introduced through the guidance tube in the housing of the endoscopic surgical device and into the cannula and advanced to visualize the A1 pulley and A2 pulley.

In the event that the tenosynovium obscures visualization of the tendon, the revolver of the device is turned to select deployment orientation of the scraper. The guiding tube is advanced along the endoscope into the cannula and the scraper protrudes through the slot of the cannula. The tenosynovium is removed with the scraper and the guiding tube is retracted, bringing the scraper back into the housing of the device. The revolver of the device is rotated to restore the scraper back to its pre-deployment configuration in the device.

The tendon is again visualized with the endoscope. The revolver of the device is turned to select deployment orientation of the blade. The guiding tube is advanced along the endoscope into the cannula and the blade protrudes through the slot of the cannula. The blade is advanced into contact with the A1 pulley. The blade is further pushed forward, dividing the A1 pulley. The guiding tube is retracted, bringing the blade back into the housing of the device. The revolver of the device is rotated to restore the blade back to its pre-deployment configuration in the device.

The cut edges of the A1 pulley and the underlying flexor tendon are visualized through the endoscope.

While visualizing the tendon, release of the tendon is confirmed by passive manipulation of the digit through its range of motion.

The absence of triggering is confirmed by having the subject flex and extend the affected digit.

The endoscope is withdrawn and the cannula is removed from the incision.

The wound is closed and a soft bandage is applied.

The patient is encouraged to begin early finger motion following surgery and to resume daily activities as tolerated.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. An endoscopic surgical device, comprising:
   (a) a housing having a proximate end and a distal end;
   (b) a slotted clear cannula attached to said distal end of said housing, said slotted clear cannula comprises a cannula body having a proximate end and a distal end, and a slot extending from said proximate end of said cannula to a proximity of said distal end of said cannula;
   (c) a rotatable assembly located within said housing, comprising:
      a slide pusher assembly comprising a notch;
      a blade comprising an upper cutting surface that forms an upper angle with a bottom surface of said blade and a lower cutting surface that forms a lower angle with the bottom surface of said blade; and
      a circular revolver body comprising a selector switch;
      wherein said blade resides at said notch of said slide pusher assembly in a pre-deployment position and wherein said selector switch allows engagement of said blade for deployment;
      wherein said blade comprises a tab that embeds into a pusher base; and
   (d) a tube assembly having a proximate end and a distal end, said distal end of said tube assembly is located within said housing and extends through said revolver body, said tube assembly connects to said slotted clear cannula from said proximate end of said clear cannula, wherein the slotted clear cannula distal to the housing has a closed end that is tapered.

2. The endoscopic surgical device of claim 1, wherein said housing further comprises a stabilizing ring that mounts into said proximate end of said housing.

3. The endoscopic surgical device of claim 1, further comprising a rotary clip that prevents said blade from sliding when in an undeployed position.

4. The endoscopic surgical device of claim 3, wherein said rotary clip comprises a tab that engages with an inside surface of said housing and an opening that allows deployment of said blade.

5. The endoscopic surgical device of claim 1, wherein said circular body of said revolver comprises a hooked tab that engages with said slide pusher assembly.

6. The endoscopic surgical device of claim 5, wherein said circular body of said revolver further comprises a set of upper tabs and a set of lower tabs, wherein said upper tabs and said lower tabs extend inwardly from an interior surface of said circular body.

7. The endoscopic surgical device of claim 1, wherein said slide pusher assembly includes a lock that comprises one or more retaining tabs that hold a rotary clip.

8. The endoscopic surgical device of claim 1, wherein said slide pusher assembly includes a lock that comprises a pair of wings that engage with said revolver.

9. The endoscopic surgical device of claim 8, wherein said slide pusher assembly includes a lock that comprises a disc at a proximate end of said lock.

10. The endoscopic surgical device of claim 1, wherein said tube assembly further comprises a tube stop at said proximate end of said tube assembly.

11. An endoscopic surgical kit, comprising the endoscopic surgical device of claim 1 and an endoscope.

12. A method for performing a uniportal endoscopic surgical procedure on
   a target tissue using the endoscopic surgical device of claim 1, comprising:
      establishing an entry portal in a subject,
      inserting into said entry portal said cannula of said endoscopic surgical device;
      extending said cannula through said entry portal to said target tissue;
      advancing an endoscope into said cannula to visualize the target tissue; and
      advancing said blade into said cannula until a desired cut is made on said target tissue.

13. The method of claim 12, wherein the uniportal endoscopic surgical procedure is selected from the group consisting of trigger linger release, carpal tunnel release, cubital tunnel release, plantar fascia release, lateral release for patella realignment, release of the extensor tendons, release of the posterior or other compartments of the leg, and forearm fascial release.

14. The endoscopic surgical device of claim 1, wherein the pusher base is curved to match a curvature of the tube assembly.

15. The endoscopic surgical device of claim 1, wherein embedding the tab into the pusher base secures the tab into the pusher base.

* * * * *